(12) United States Patent
Chopra

(10) Patent No.: US 7,527,754 B2
(45) Date of Patent: *May 5, 2009

(54) PHOTOCHROMIC INDENO-FUSED NAPHTHOPYRANS

(75) Inventor: Anu Chopra, Pittsburgh, PA (US)

(73) Assignee: Transitions Optical, Inc., Pinellas Park, FL (US)

( * ) Notice: Subject to any disclaimer, the term of this patent is extended or adjusted under 35 U.S.C. 154(b) by 388 days.

This patent is subject to a terminal disclaimer.

(21) Appl. No.: 11/314,142

(22) Filed: Dec. 21, 2005

(65) Prior Publication Data

US 2007/0138448 A1 Jun. 21, 2007

(51) Int. Cl.
*F21V 9/00* (2006.01)
*G02B 5/02* (2006.01)
*G02C 7/10* (2006.01)
*G02F 1/361* (2006.01)
*G03B 11/00* (2006.01)

(52) U.S. Cl. ............... 252/582; 549/356; 549/382; 544/149

(58) Field of Classification Search ......... 252/582–589; 428/412, 424.2, 441, 442, 461–463, 500–523
See application file for complete search history.

(56) References Cited

U.S. PATENT DOCUMENTS

| 5,645,767 | A | * | 7/1997 | Van Gemert | ............... | 252/586 |
| 6,025,026 | A | | 2/2000 | Smith et al. | ............... | 427/316 |
| 6,068,797 | A | | 5/2000 | Hunt | ............... | 264/1.7 |
| 6,113,814 | A | | 9/2000 | Gemert et al. | ............... | 252/586 |
| 6,150,430 | A | | 11/2000 | Walters et al. | ............... | 522/79 |
| 6,296,785 | B1 | * | 10/2001 | Nelson et al. | ............... | 252/586 |
| 6,555,028 | B2 | | 4/2003 | Walters et al. | ............... | 252/586 |
| 2001/0025948 | A1 | * | 10/2001 | Walters et al. | ............... | 252/586 |
| 2003/0165686 | A1 | | 9/2003 | Blackburn et al. | ............... | 428/412 |
| 2005/0151926 | A1 | | 7/2005 | Kumar et al. | ............... | 351/163 |
| 2005/0258408 | A1 | | 11/2005 | Molock et al. | | |
| 2006/0226400 | A1 | * | 10/2006 | Xiao et al. | ............... | 252/582 |
| 2006/0226401 | A1 | * | 10/2006 | Xiao et al. | ............... | 252/586 |
| 2006/0226402 | A1 | * | 10/2006 | Kim et al. | ............... | 252/586 |
| 2007/0138449 | A1 | * | 6/2007 | Chopra et al. | ............... | 252/586 |

FOREIGN PATENT DOCUMENTS

| EP | 1 016 702 A2 | 7/2000 |
| WO | WO 01/70719 A2 | 9/2001 |
| WO | WO 2006/022825 A1 | 3/2006 |
| WO | WO 2006/110219 A1 | 10/2006 |
| WO | WO 2006/110520 A1 | 10/2006 |

OTHER PUBLICATIONS

Lange's Handbook of Chemistry, McGraw Hill, 15th Edition, 1999, pp. 9.1-9.8, J. A. Dean, "Section 9 Physiocochemical Relationships".

* cited by examiner

*Primary Examiner*—Lorna M Douyon
*Assistant Examiner*—Bijan Ahvazi
(74) *Attorney, Agent, or Firm*—Linda Pingitore; Frank P. Mallak; Deborah M. Altman

(57) ABSTRACT

Photochromic materials comprising indeno-fused naphthopyrans having substituents comprising a 4-fluorophenyl group and a 4-aminophenyl group bonded to the 3-position of the indeno-fused naphthopyran are disclosed. The photochromic materials may exhibit faster fade rates as compared to similar indeno-fused naphthopyrans without a 4-fluorophenyl group and a 4-aminophenyl group bonded to the 3-position of the indeno-fused naphthopyran. Substituted 2-propyn-1-ols utilized for the synthesis of the indeno-fused naphthopyrans disclosed herein are disclosed. Photochromic compositions and articles, such as optical elements, incorporating the photochromic materials disclosed herein are also disclosed.

14 Claims, 2 Drawing Sheets

PHOTOCHROMIC INDENO-FUSED NAPHTHOPYRANS

BACKGROUND

Various non-limiting embodiments of the present disclosure related to photochromic materials comprising indeno-fused naphthopyrans having substituents comprising a 4-fluorophenyl and a 4-aminophenyl group bonded to the 3-position of the naphthopyran. The photochromic materials according to various non-limiting embodiments of the present disclosure may also exhibit faster fade rates as compared to similar indeno-fused naphthopyrans without a 4-fluorophenyl and a 4-aminophenyl group bonded to the 3-position of the naphthopyran. Other non-limiting embodiments of the present disclosure also relates to substituted 2-propyn-1-ols for the synthesis of the indeno-fused naphthopyrans disclosed herein. Still other non-limiting embodiments disclosed herein relate to photochromic compositions and articles, such as optical elements, incorporating the photochromic materials.

Many conventional photochromic materials, such as, for example, photochromic naphthopyrans, can undergo a transformation from a first form or state to a second form or state in response to the absorption of electromagnetic radiation. For example, many conventional thermally reversible photochromic materials are capable of transforming between a first "clear" or "bleached" ground-state form and a second "colored" activated-state form in response to the absorption of certain wavelengths of electromagnetic radiation (or "actinic radiation"). As used herein the term "actinic radiation" refers to electromagnetic radiation that is capable of causing a photochromic material to transform from a first form or state to a second form or state. The photochromic material may then revert back to the clear ground-state form in response to thermal energy in the absence of actinic radiation. Photochromic articles and compositions that contain one or more photochromic materials, for example, photochromic lenses for eyewear applications, generally display optically clear and colored states that correspond to the photochromic material(s) that they contain. Thus, for example, eyewear lenses that contain photochromic materials can transform from a clear state to a colored state upon exposure to actinic radiation, such as certain wavelengths found in sunlight, and can revert back to the clear state in the absence of such radiation upon absorption of thermal energy.

When utilized in photochromic articles and compositions, conventional photochromic materials are typically incorporated into a host polymer matrix by one of imbibing, blending, and/or bonding. Alternatively, the photochromic material may be imbibed into a pre-formed article or coating. As used herein, the term "photochromic composition" refers to a photochromic material in combination with one or more other material, which may or may not be a photochromic material.

For many photochromic applications, it is generally desirable to have a photochromic material that can rapidly revert from the colored, activated-state form to the clear, ground-state form, while still maintaining acceptable characteristics such as color density. For example, in photochromic eyewear applications, optical lenses comprising photochromic materials transform from an optically clear state to a colored state as the wearer moves from a region of low actinic radiation, such as indoors, to a region of high actinic radiation, such as into direct sunlight. As the lenses become colored, less electromagnetic radiation from the visible and/or ultraviolet regions of the electromagnetic spectrum is transmitted through the lens to the wearer's eyes. In other words, more electromagnetic radiation is absorbed by the lens in the colored state than in the optically clear state. When the wearer subsequently moves from the region of high actinic radiation back to a region of low actinic radiation, the photochromic materials in the eyewear revert from the colored, activated-state form to the clear, ground-state form in response to thermal energy. If this transformation from colored to clear takes several minutes or more, the wearer's vision may be less than optimal during this time due to the combined effect of the lower ambient light and the reduced transmission of visible light through the colored lenses.

Accordingly, for certain applications, it may be advantageous to develop photochromic materials that can more quickly transition from the colored form to the clear form, as compared to conventional photochromic materials. As used herein, the term "fade rate" is a measurement of the rate at which the photochromic material transforms from the activated colored state to the unactivated clear state. The fade rate for a photochromic material may be measured, for example, by activating a photochromic material to saturation under controlled conditions in a given matrix, measuring its activated steady state absorbance (i.e., saturated optical density) and then determining the length of time it takes for the absorbance of the photochromic material to decrease to one-half the activated steady state absorbance value. As measured in this fashion, the fade rate is designated by $T_{1/2}$, with units of seconds.

The absorption spectrum of a photochromic material in the activated-state form will correspond to the color of the article containing the photochromic material, for example, the color of the eyewear lens, when exposed to actinic radiation. As specific wavelengths within the visible region of electromagnetic radiation are absorbed by a photochromic material in the activated-state form, the wavelengths within the visible region that are transmitted (i.e., not absorbed) correspond to the color of the photochromic material in the open form. Absorption of wavelengths of light around about 500 nm to about 520 nm in the visible region of the electromagnetic spectrum results in a photochromic material that exhibits a "reddish" color, i.e., it absorbs visible radiation from the short wavelength or blue end of the visible spectrum and transmits radiation from the longer wavelength or red end of the visible spectrum. Conversely, absorption of wavelengths of light around about 580 nm to about 610 nm in the visible region of the electromagnetic spectrum results in a photochromic material that exhibits a "bluer" color, i.e., it absorbs visible radiation from the longer wavelength or red end of the visible spectrum and transmits radiation from the shorter wavelength or blue end of the visible spectrum.

Many current photochromic compounds have activated-state absorption spectrums that absorb visible light toward the blue end of the visible spectrum and exhibit a reddish color in the activated form. If the photochromic material has an activated-state absorption spectrum that is bathochromically shifted, i.e., shifted to absorb light having a longer wavelength, the photochromic material will exhibit a bluer color than the current photochromic material. For certain applications it may be desirable to have a photochromic material that has a bathochromically shifted activated form absorption spectrum for actinic radiation and which may therefore exhibit a bluer color.

BRIEF SUMMARY

Various non-limiting embodiments disclosed herein relate to photochromic materials comprising indeno-fused naphthopyrans having substituents comprising a 4-fluorophenyl and a 4-aminophenyl group bonded to the 3-position of the indeno-fused naphthopyran. Photochromic materials according to certain non-limiting embodiments may have faster fade rates than a comparable photochromic indeno-fused naphthopyran that does not have substituents comprising a 4-fluorophenyl and a 4-aminophenyl group bonded to the 3-position of the indeno-fused naphthopyran.

In one non-limiting embodiment, the photochromic material may comprise an indeno-fused naphthopyran comprising a group B attached to the 3-position thereof and a group B' attached to the 3-position thereof. The group B may be a 4-fluorophenyl group and the group B' may be a 4-substituted phenyl group, wherein the substituent in the 4-position of the 4-substituted phenyl group is —NR$^1$R$^2$, wherein R$^1$ and R$^2$ are each independently hydrogen, $C_1$-$C_6$ alkyl, $C_5$-$C_7$ cycloalkyl, phenyl, mono-substituted phenyl, or di-substituted phenyl, wherein said phenyl substituents are $C_1$-$C_6$ alkyl or $C_1$-$C_6$ alkoxy, or R$^1$ and R$^2$ come together with the nitrogen atom to form a nitrogen containing ring represented by the following graphic formula II:

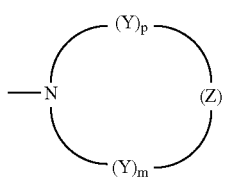

II wherein each —Y— is independently chosen for each occurrence from —CH$_2$—, —CH(R$^3$)—, —C(R$^3$)$_2$—, —CH(aryl)-, —C(aryl)$_2$-, and —C(R$^3$)(aryl)-, and Z is —Y—, —O—, —S—, —S(O)—, —SO$_2$—, —NH—, —N(R$^3$)—, or —N(aryl)-, wherein each R$^3$ is independently $C_1$-$C_6$ alkyl, or hydroxy($C_1$-$C_6$)alkyl, each aryl is independently phenyl or naphthyl, m is an integer 1, 2 or 3, and p is an integer 0, 1, 2, or 3 and when p is 0, Z is —Y—.

Still further non-limiting embodiments of the present disclosure relate to a photochromic material having the structure as set forth in structure III:

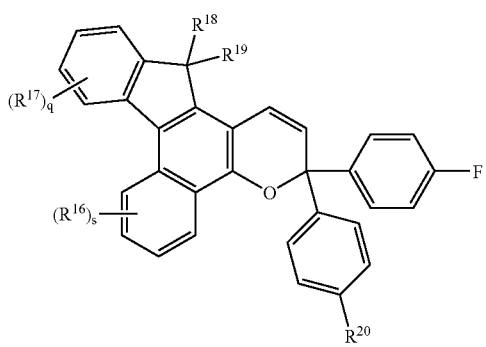

III wherein R$^{16}$, R$^{17}$, R$^{18}$, R$^{19}$, and R$^{20}$ represent groups as described herein below and set forth in the claims.

Still further non-limiting embodiments of the present disclosure relate to a chemical compound having the structure as set forth in structure VI:

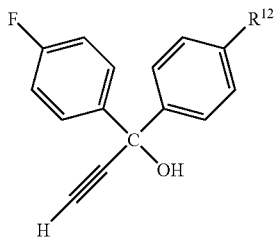

VI wherein R$^{12}$ represents a group as described herein and set forth in the claims. Still further non-limiting embodiments of the present disclosure relate to a method of making a photochromic material comprising reacting the compound of figure VI with a 7H-benzo[C]fluoren-5-ol to form a 3H,13H-indeno [2',3':3,4]naphtho[1,2-b]pyran.

Other non-limiting embodiments relate to photochromic articles comprising a substrate and the photochromic material according to any of the non-limiting embodiments disclosed herein.

BRIEF DESCRIPTION OF THE DRAWINGS

The various non-limiting embodiments disclosed herein may be better understood when read in conjunction with the following Figures.

DETAILED DESCRIPTION

Figure 1:
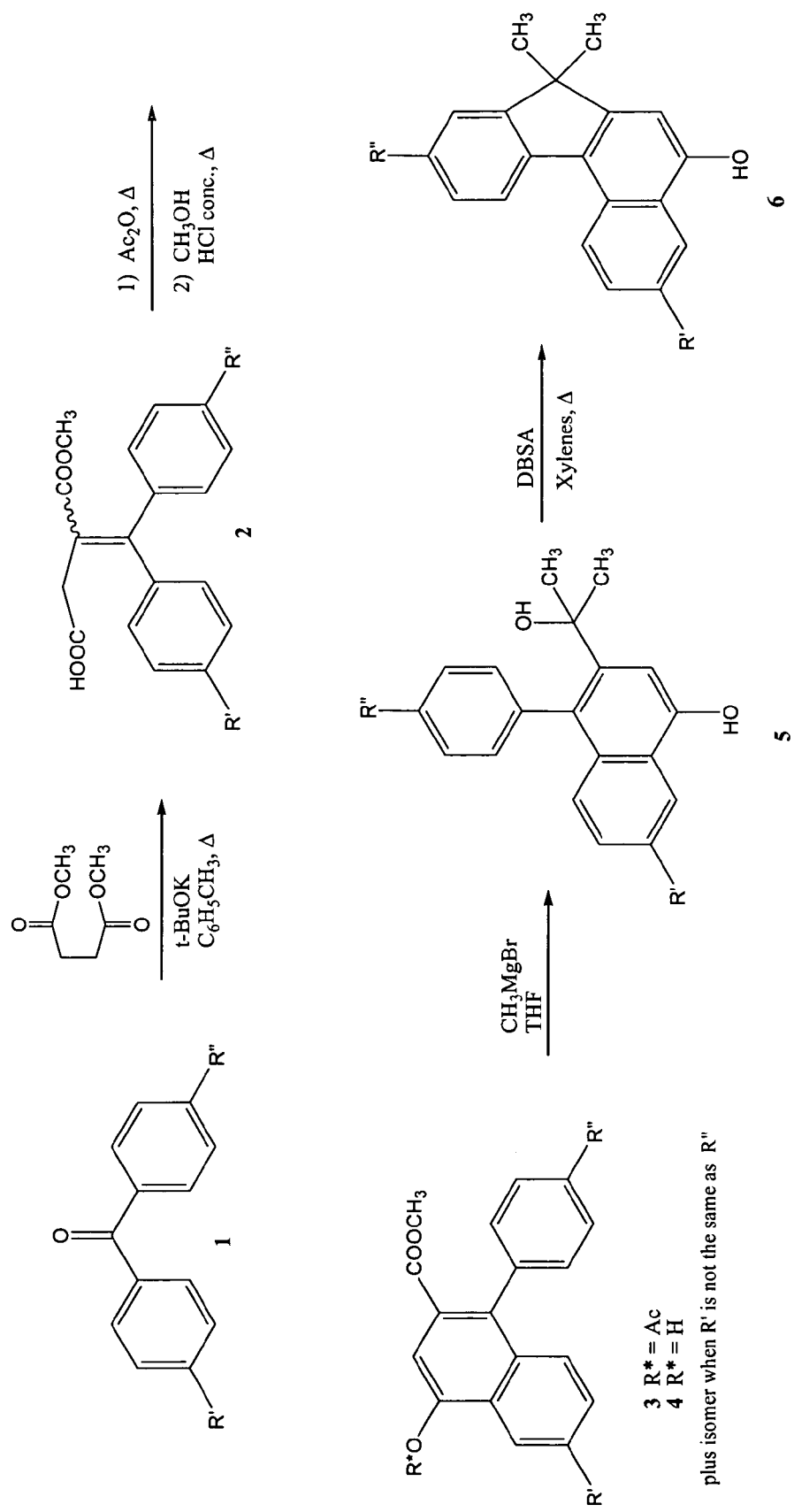
FIGS. 1-2 illustrate schematic diagrams of reaction schemes for making intermediates for the synthesis of the photochromic materials according to various non-limiting embodiments disclosed herein.

As used in this specification and the appended claims, the articles "a," "an," and "the" include plural referents unless expressly and unequivocally limited to one referent.

Additionally, for the purposes of this specification, unless otherwise indicated, all numbers expressing quantities of ingredients, reaction conditions, and other properties or parameters used in the specification are to be understood as being modified in all instances by the term "about." Accordingly, unless otherwise indicated, it should be understood that the numerical parameters set forth in the following specification and attached claims are approximations. At the very least, and not as an attempt to limit the application of the doctrine of equivalents to the scope of the claims, numerical parameters should be read in light of the number of reported significant digits and the application of ordinary rounding techniques.

Further, while the numerical ranges and parameters setting forth the broad scope of the invention are approximations as discussed above, the numerical values set forth in the Examples section are reported as precisely as possible. It should be understood, however, that such numerical values inherently contain certain errors resulting from the measurement equipment and/or measurement technique.

Photochromic compounds and materials according to the various non-limiting embodiments of the invention will now be discussed. As used herein, the term "photochromic" means having an absorption spectrum for at least visible radiation that varies in response to absorption of at least actinic radiation. As used herein the term "actinic radiation" refers to electromagnetic radiation that is capable of causing a photochromic material to transform from a first form or state to a second form or state. Further, as used herein, the term "photochromic material" means any substance that is adapted to display photochromic properties, i.e., adapted to have an absorption spectrum for at least visible radiation that varies in response to absorption of at least actinic radiation. As used herein, the term "photochromic composition" refers to a photochromic material in combination with one or more other material, which may or may not be a photochromic material.

As used herein, the term "indeno-fused naphthopyran" is defined as a photochromic compound having a ring skeleton comprising an indeno [2',3':3,4]naphtho[1,2-b]pyran, as shown below in (I). Indeno-fused naphthopyrans are examples of photochromic naphthopyrans. As used herein, the term "photochromic naphthopyrans" refers to naphthopyrans that are capable of transforming between a first "closed-form" and a second "open-form" in response to the absorption of actinic radiation. As used herein, the term "closed-form" corresponds to the ground-state form of the indeno-fused naphthopyran and the term "open-form" corresponds to the activated-state form of the indeno-fused naphthopyran.

As used herein, the terms "3-position," "6-position," "11-position," and so forth refer to the 3-, 6-, and 11-position respectively of the ring atoms of the indeno-fused naphthopyran skeleton, as illustrated by the numbered positions on structure (I) below. Further, the rings of the indeno-fused naphthopyran skeleton may be denoted by a letter from A to E, such that each ring may be referred to by its corresponding letter. Thus for example, as used herein, the terms "C ring" or "C ring of the indeno-fused naphthopyran" correspond to the lower ring of the naphthyl substructure of the indeno-fused naphthopyran, as denoted by the ring labeled "C" in structure (I) below. As used herein, the term "bonded to a carbon of the C ring" means bonded to a carbon in at least one of the 5-position, the 6-position, the 7-position, or the 8-position, according to the numbering set forth in structure (I).

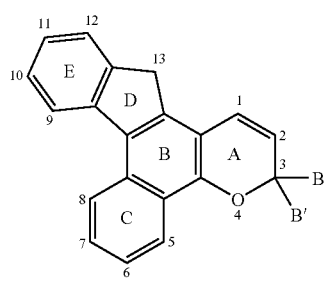

I

According to various non-limiting embodiments disclosed herein, the groups B and B' at the 3-position of the indeno-fused naphthopyran are part of the photochromic indeno-fused naphthopyran skeleton illustrated above in (I). Without intending to be limited by any particular theory, it is believed that the B and B' groups may help stabilize the open form of the indeno-fused naphthopyran structure. According to various non-limiting embodiments disclosed herein, the groups B and/or B' may be any structures that have at least one pi-bond capable of being in conjugation with the pi-system of the open-form of the core indeno-fused naphthopyran structure, such as, in the various non-limiting embodiments of the present disclosure, a substituted phenyl substituent. According to various non-limiting embodiments of the present disclosure, the B and B' groups of the photochromic materials may each comprise a 4-substituted phenyl group, wherein the substituent in the 4-position of each 4-substituted phenyl group of the B and B' groups are as set forth herein below.

Various non-limiting embodiments of the photochromic materials of the present disclosure will now be discussed in detail. According to certain non-limiting embodiments, the present disclosure provides for a photochromic material comprising an indeno-fused naphthopyran comprising a group B attached to the 3-position of the indeno-fused naphthopyran and a group B' attached to the 3-position of the indeno-fused naphthopyran. The group B may be a 4-fluorophenyl group and the group B' may be a 4-substituted phenyl group, wherein the substituent in the 4-position of the 4-substituted phenyl group is —NR$^1$R$^2$. According to various non-limiting embodiments, R$^1$ and R$^2$ may each independently be: hydrogen, $C_1$-$C_6$ alkyl, $C_5$-$C_7$ cycloalkyl, phenyl, mono-substituted phenyl, or di-substituted phenyl, wherein said phenyl substituents may be $C_1$-$C_6$ alkyl or $C_1$-$C_6$ alkoxy, or R$^1$ and R$^2$ may come together with the nitrogen atom to form a nitrogen containing ring represented by the following graphic formula II:

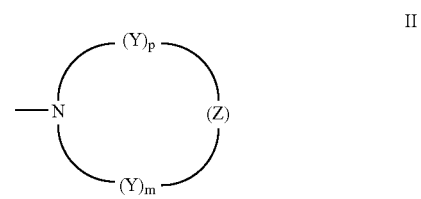

II wherein each —Y— may independently be chosen for each occurrence from —CH$_2$—, —CH(R$^3$)—, —C(R$^3$)$_2$—, —CH(aryl)-, —C(aryl)$_2$-, and —C(R$^3$)(aryl)-, and Z is —Y—, —O—, —S—, —S(O)—, —SO$_2$—, —NH—, —N(R$^3$)—, or —N(aryl)-, wherein each R$^3$ is independently $C_1$-$C_6$ alkyl, or hydroxy($C_1$-$C_6$)alkyl, each aryl may independently be phenyl or naphthyl, 'm' is an integer 1, 2 or 3, and 'p' is an integer 0, 1, 2, or 3 and when 'p' is 0, Z is —Y—.

According to certain non-limiting embodiments, the photochromic materials may have a faster fade rate, as measured in a polymethacrylate chip, than a comparable photochromic material comprising an indeno-fused naphthopyran wherein the indeno-fused naphthopyran lacks a 4-fluorophenyl group attached to the 3-position thereof and a 4-substituted phenyl at the 3-position, wherein the substituent at the 4-position of the 4-substituted phenyl is —NR$^1$R$^2$.

As used throughout the present disclosure, the term "fade rate" represents a kinetic rate value that may be expressed by measuring the $T_{1/2}$ value of the photochromic material. As used herein, the term "fade rate" is a measurement of the rate at which the photochromic material transforms from the activated colored state to the unactivated clear state. The fade rate for a photochromic material may be measured, for example, by activating a photochromic material to saturation under controlled conditions in a given matrix, measuring its activated steady state absorbance (i.e., saturated optical density) and then determining the length of time it takes for the absorbance of the photochromic material to decrease to one-half the activated steady state absorbance value. As measured in this fashion, the fade rate is designated by $T_{1/2}$, with the units of seconds. Thus, when the fade rate is said to be "faster," the photochromic compound changes from the colored activated-state to the clear ground-state at a faster rate. The faster fade rate may be indicated, for example, by a decrease in value of the $T_{1/2}$ measurement for the photochromic material. That is, as the fade rate becomes faster, the length of time for the absorbance to decrease to one-half the initial activated absorbance value will become shorter. More detailed measurement procedures for determining the $T_{1/2}$ values for the photochromic materials disclosed herein, are set forth in the Examples below.

It will be appreciated by those skilled in the art that the fade rate of the photochromic material may be dependent on the media into which the photochromic material is incorporated. As used herein, the term "incorporated" when used in relation to a photochromic material is a media means physically and/or chemically combined with. In the present disclosure, all photochromic performance data disclosed herein, for example, fade rate ($T_{1/2}$), maximum absorbance wavelength ($\lambda_{max-vis}$), saturated optical density, and performance rating, are measured using a standard protocol involving incorporation of the photochromic material in a polymer test chip comprising a methacrylate polymer, unless specifically noted otherwise. As used herein, the terms "maximum absorbance wavelength" or "$\lambda_{max-vis}$" is the wavelength in the visible spectrum at which the maximum absorbance of the activated (colored) form of the photochromic material is observed. As used herein, the term "saturated optical idensity" (abbreviated "Sat'd OD"), is a measurement of the steady state absorbance (i.e., optical density) of the activated photochromic material under standard conditions as defined in the Examples. As used herein, the term "performance rating" or "PR" is a measurement of the performance of a photochromic material and is calculated by the equation:

Performance Rating=((Sat'd OD)/$T_{1/2}$)×10,000.

Performance ratings typically have values from 1 to 100, with higher values generally being preferred.

Photochromic performance testing and the standard protocol for formation of the polymer test chip, which incorporates the photochromic materials of the various non-limiting embodiments of the present disclosure, are disclosed in greater detail in the Examples section herein. One skilled in the art will recognize that although exact values for fade rates and other photochromic performance data may vary depending on the media of incorporation, the photochromic performance data disclosed herein may be illustrative of relative rates and data values to be expected for the photochromic material when incorporated in other media.

According to other non-limiting embodiments, the photochromic material comprises an indeno-fused naphthopyran where the B group may be a 4-fluorophenyl group and the B' group may be a 4-morpholinophenyl, a 4-piperidinophenyl, a 4-(substituted piperidino)phenyl, a 4-pyrrolidinophenyl, a 4-(substituted pyrrolidino)phenyl, or a 4-piperazinophenyl, wherein the substituent may be $C_1$-$C_6$ alkyl or hydroxy($C_1$-$C_6$)alkyl. In certain non-limiting embodiments, the 4-piperazinophenyl may be a 4-(N'-substituted)piperazinophenyl, wherein the substitution on the nitrogen may be a $C_1$-$C_6$ alkyl substituent. According to still further non-limiting embodiments, the B' group may be a 4-(N,N-dialkylamino)phenyl, wherein the alkyl groups may be the same or different and may be $C_1$-$C_6$ alkyl, such as, for example, methyl, ethyl, propyl, isopropyl, and butyl.

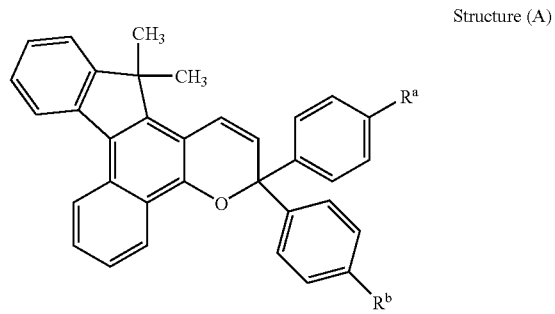

Structure (A)

A1 $R^a$ = F, $R^b$ = piperidino
A2 $R^a$ = F, $R^b$ = morpholino
A3 $R^a$ = H, $R^b$ = H
A4 $R^a$ = H, $R^b$ = piperidino
A5 $R^a$ = H, $R^b$ = morpholino
A6 $R^a$ = F, $R^b$ = H According to certain non-limiting embodiments disclosed herein, the photochromic materials comprising an indeno-fused naphthopyran having a B group comprising a 4-fluorophenyl and a B' group comprising a 4-aminophenyl, as set forth and claimed herein, may have a fade rate, as measured by a $T_{1/2}$ value, that is faster than a comparable indeno-fused naphthopyran without the combined B and B' groups as set forth above. For example and with reference to Structure (A), compound A1, according to one specific non-limiting embodiment, the photochromic material wherein the B group is a 4-fluorophenyl ($R^a$=F) and the B' group is a 4-piperidinophenyl ($R^b$=piperidino) has a fade rate of $T_{1/2}$=118 seconds. In contrast and with reference to Structure (A), compounds A3 and A4, two comparable photochromic material where the B group is phenyl ($R^a$=H) and the B' group is either phenyl ($R^b$=H) or 4-piperidinophenyl ($R^b$=piperidino), respectively, have slower fade rate $T_{1/2}$ values of 723 seconds and 180 seconds, respectively. In addition, with reference to Structure (A), compound A6, the comparable photochromic material where the B group is 4-fluorophenyl ($R^a$=F) and the B' group is phenyl ($R^b$=H) has a slower fade rate $T_{1/2}$ value of 542 seconds.

Further, with reference to Structure (A), compound A2, according to another specific non-limiting embodiment, the photochromic material wherein the B group is a 4-fluorophenyl ($R^a$=F) and the B' group is a 4-morpholinophenyl ($R^b$=morpholino) has a fade rate of $T_{1/2}$=151 seconds. In contrast and with reference to Structure (A), compounds A3 and A5, two comparable photochromic material where the B group is phenyl ($R^a$=H) and the B' group is either phenyl ($R^b$=H) or 4-morpholinophenyl ($R^b$=morpholino), respectively, have slower fade rate $T_{1/2}$ values of 723 seconds and 241 seconds, respectively. In addition, with reference to Structure (A), compound A6, the comparable photochromic material where the B group is 4-fluorophenyl ($R^a$=F) and the B' group is phenyl ($R^b$=H) has a slower fade rate $T_{1/2}$ value of 542 seconds.

Certain non-limiting embodiments of the photochromic materials may comprise, in addition to the B and B' groups as described herein, a first electron-withdrawing group bonded to a carbon of the C-ring of the indeno-fused naphthopyran. According to certain non-limiting embodiments of the photochromic material, the first electron-withdrawing group may be bonded to the 6-position of the C-ring of the indeno-fused naphthopyran.

As used herein, the terms "group" or "groups" mean an arrangement of one or more atoms. As used herein, the term "electron-withdrawing group" may be defined as a group that withdraws electron density from a pi-system, such as, for example, the pi-system of the indeno-fused naphthopyran skeleton. Further, an "electron-withdrawing group", as used herein, may be defined as a group having a positive Hammett $\sigma_p$ value, when the group is attached to a carbon participating in an aromatic pi-system, such as the aromatic pi-system of the indeno-fused naphthopyran core. As used herein, the term "Hammett $\sigma_p$ value" is a measurement of the electronic influence, as either an electron-donating or electron-withdrawing influence, of a substituent attached to a carbon participating in an aromatic pi system that is transmitted through the polarizable pi electron system, such as, for example, an aromatic pi electron system. The Hammett $\sigma_p$ value is a relative measurement comparing the electronic influence of the substituent in the para position of a phenyl ring to the electronic influence of a hydrogen substituted at the para position. Typically for aromatic substituents in general, a negative Hammett $\sigma_p$ value is indicative of a group or substituent having an electron-donating influence on a pi electron system (i.e., an electron-donating group) and a positive Hammett $\sigma_p$ value is indicative of a group or substituent having an electron-withdrawing influence on a pi electron system (i.e., an electron-withdrawing group).

Electron-withdrawing groups suitable for use in connection with various non-limiting embodiments of the photochromic material described herein may have a Hammett $\sigma_p$ value ranging from about 0.05 to about 0.75. Suitable electron-withdrawing groups may comprise, for example and without limitation: halogen, such as fluoro ($\sigma_p$=0.06), chloro ($\sigma_p$=0.23), and bromo ($\sigma_p$=0.23); perfluoroalkyl (for example, —CF$_3$, $\sigma_p$=0.54) or perfluoroalkoxy (for example, —OCF$_3$, $\sigma_p$=0.35), where the perfluoroalkyl portion of either the perfluoroalkyl or the perfluoroalkoxy may comprise, for example, trifluoromethyl or other perfluoroalkyl portions having the formula $C_nF_{2n+1}$, where 'n' is an integer from 1 to 10; cyano ($\sigma_p$=0.66); —OC(=O)R$^4$ (for example, —OC(=O)CH$_3$, $\sigma_p$=0.31); —SO$_2$X (for example, —SO$_2$CH$_3$, $\sigma_p$=0.68); or —C(=O)—X, where X is hydrogen (—CHO, $\sigma_p$=0.22), $C_1$-$C_6$ alkyl (for example, —C(=O)CH$_3$, $\sigma_p$=0.50), —OR$^5$ ($\sigma_p$≈0.4), or —NR$^6$R$^7$ (for example, —C(=O)NH$_2$, $\sigma_p$=0.36), wherein each of R$^4$, R$^5$, R$^6$, and R$^7$ may each independently be hydrogen, $C_1$-$C_6$ alkyl, $C_5$-$C_7$ cycloalkyl, phenyl, mono-substituted phenyl, di-substituted phenyl, alkylene glycol, or polyalkylene glycol, wherein the phenyl substituents may be $C_1$-$C_6$ alkyl or $C_1$-$C_6$ alkoxy. Further suitable electron-withdrawing substituents having Hammett $\sigma_p$ values in the range from about 0.05 to about 0.75 are set forth in "Section 9 Physicochemical Relationships" in *Lange's Handbook of Chemistry*, 15$^{th}$ ed. J. A. Dean, editor, McGraw Hill, 1999, pp 9.1-9.8, the disclosure of which is incorporated herein by reference. It will be appreciated by those skilled in the art that the subscript "p", when used in connection with the Hammett $\sigma$ value, refers to the Hammett $\sigma_p$ value as measured when the group is located at the para position of a phenyl ring of a model system, such as a para-substituted benzoic acid model system.

As used herein, the term "polyalkylene glycol" means a substituent having the general structure of —[O—($C_aH_{2a}$)]$_b$—OR", where 'a' and 'b' are each independently integers from 1 to 10, and R" may be H, alkyl, a reactive substituent, or a second photochromic material. Non-limiting examples of suitable polyalkylene glycols may be found in U.S. Pat. No. 6,113,814, column 3, lines 30-64, which disclosure is incorporated herein by reference. Non-limiting examples of reactive substituents may be found in U.S. patent application Ser. No. 11/102,280, paragraphs [0033]-[0040], which disclosure is incorporated herein by reference.

According to further non-limiting embodiments, the photochromic materials of the present disclosure may further comprise a second electron-withdrawing group bonded to the 11-position of the indeno-fused naphthopyran. According to various non-limiting embodiments, the second electron-withdrawing group may be fluoro, chloro, bromo, perfluoroalkyl, perfluoroalkoxy, cyano, —OC(=O)R$^8$, —SO$_2$X, or —C(=O)—X, X is hydrogen, $C_1$-$C_6$ alkyl, —OR$^9$, or —NR$^{10}$R$^{11}$, wherein R$^8$, R$^9$, R$^{10}$, and R$^{11}$ are each independently hydrogen, $C_1$-$C_6$ alkyl, $C_5$-$C_7$ cycloalkyl, phenyl, mono-substituted phenyl, or di-substituted phenyl, wherein said phenyl substituents are $C_1$-$C_6$ alkyl or $C_1$-$C_6$ alkoxy.

Further discussion of photochromic material comprising an indeno-fused naphthopyran, a first electron-withdrawing group, and, in certain non-limiting embodiments, a second electron-withdrawing group, as set forth above, may be found in U.S. Non-provisional application Ser. No. 11/314,141, (publication number 2007/0138449 A1), entitled "Photochromic Materials Having Electron-Withdrawing Substituents", filed concurrently herewith, the disclosure of which is incorporated by reference in its entirety.

According to certain non-limiting embodiments, the photochromic materials of the present disclosure may comprise an indeno-fused naphthopyran wherein the first electron-withdrawing group bonded to the 6-position thereof may be a first fluoro group and the second electron-withdrawing group bonded to the 11-position thereof may be a second fluoro group.

According to other non-limiting embodiments, the photochromic materials of the present disclosure have the structure represented by formula (III), below.

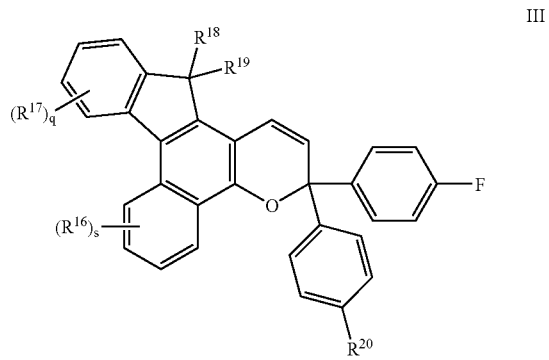

With reference to structure (III), 's' may be an integer ranging from 0 to 3 and 'q' may be an integer ranging from 0 to 3. Each R$^{16}$ and each R$^{17}$ may for each occurrence comprise, for example, hydrogen; fluoro; chloro; bromo; perfluoroalkyl; perfluoroalkoxy; cyano; —OC(=O)R$^{21}$; —SO$_2$X; —C(=O)—X, wherein X may be, for example, hydrogen, $C_1$-$C_6$ alkyl, —OR$^{22}$, or —NR$^{23}$R$^{24}$, wherein R$^{21}$, R$^{22}$, R$^{23}$, and R$^{24}$ may each independently be hydrogen, $C_1$-$C_6$ alkyl, $C_5$-$C_7$ cycloalkyl, phenyl, mono-substituted phenyl, or di-substituted phenyl, wherein said phenyl substituents may be $C_1$-$C_6$ alkyl or $C_1$-$C_6$ alkoxy; $C_1$-$C_6$ alkyl; $C_3$-$C_7$ cycloalkyl; substituted or unsubstituted phenyl; —OR$^{25}$, wherein R$^{25}$ may be, for example, hydrogen, $C_1$-$C_6$ alkyl, phenyl($C_1$-$C_3$)

alkyl, mono($C_1$-$C_6$)alkyl substituted phenyl($C_1$-$C_3$)alkyl, mono($C_1$-$C_6$)alkoxy substituted phenyl($C_1$-$C_3$)alkyl, ($C_1$-$C_6$)alkoxy($C_2$-$C_4$)alkyl, $C_3$-$C_7$ cycloalkyl, or mono($C_1$-$C_4$) alkyl substituted $C_3$-$C_7$ cycloalkyl, and said phenyl substituents may be $C_1$-$C_6$ alkyl or $C_1$-$C_6$ alkoxy; a mono-substituted phenyl, said phenyl having a substituent located at the para position, wherein the substituent is: a dicarboxylic acid residue or derivative thereof, a diamine residue or derivative thereof, an amino alcohol residue or derivative thereof, a polyol residue or a derivative thereof, —$CH_2$—, —$(CH_2)_t$—, or —$[O—(CH_2)_t]_k$—, wherein 't' is the integer 2, 3, 4, 5 or 6 and 'k' is an integer from 1 to 50, the substituent being connected to an aryl group on another photochromic material; or —$N(R^{26})R^{27}$, wherein $R^{26}$ and $R^{27}$ may each independently be, for example, hydrogen, $C_1$-$C_8$ alkyl, phenyl, naphthyl, furanyl, benzofuran-2-yl, benzofuran-3-yl, thienyl, benzothien-2-yl, benzothien-3-yl, dibenzofuranyl, dibenzothienyl, benzopyridyl, fluorenyl, $C_1$-$C_8$ alkylaryl, $C_3$-$C_{20}$ cycloalkyl, $C_4$-$C_{20}$ bicycloalkyl, $C_5$-$C_{20}$ tricycloalkyl or $C_1$-$C_{20}$ alkoxyalkyl, wherein said aryl group is phenyl or naphthyl. Alternatively, $R^{26}$ and $R^{27}$ may come together with the nitrogen atom to form a $C_3$-$C_{20}$ hetero-bicycloalkyl ring or a $C_4$-$C_{20}$ hetero-tricycloalkyl ring; a nitrogen containing ring represented by the following graphic formula IVA:

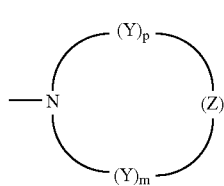

IVA wherein each —Y— may independently be for each occurrence —$CH_2$—, —$CH(R^{28})$—, —$C(R^{28})_2$—, —$CH(aryl)$-, —$C(aryl)_2$-, or —$C(R^{28})(aryl)$-, and Z may be —Y—, —O—, —S—, —S(O)—, —$SO_2$—, —NH—, —$N(R^{28})$—, or —N(aryl)-, wherein each $R^{28}$ may independently be $C_1$-$C_6$ alkyl or hydroxy($C_1$-$C_6$)alkyl, each aryl may independently be phenyl or naphthyl, 'm' is an integer 1, 2 or 3, and 'p' is an integer 0, 1, 2, or 3 and when 'p' is 0, Z is —Y—; a group represented by one of the following graphic formulae IVB or IVC:

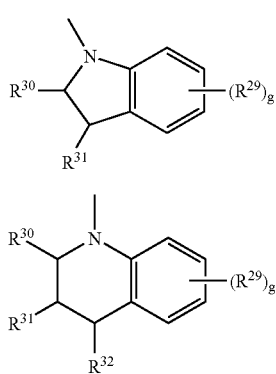

wherein $R^{30}$, $R^{31}$, and $R^{32}$ may each independently be, for example, hydrogen, $C_1$-$C_6$ alkyl, phenyl, or naphthyl, or the groups $R^{30}$ and $R^{31}$ may together form a ring of 5 to 8 carbon atoms and each $R^{29}$ may independently for each occurrence be $C_1$-$C_6$ alkyl, $C_1$-$C_6$ alkoxy, fluoro or chloro and 'g' is an integer 0, 1, 2, or 3; or an unsubstituted, mono-, or di-substituted $C_4$-$C_{18}$ spirobicyclic amine, or an unsubstituted, mono-, and di-substituted $C_4$-$C_{18}$ spirotricyclic amine, wherein said substituents are independently aryl, $C_1$-$C_6$ alkyl, $C_1$-$C_6$ alkoxy, or phenyl($C_1$-$C_6$)alkyl. Further, an $R^{16}$ group in the 6-position and an $R^{16}$ group in the 7-position together may form a group represented by one of IVD and IVE:

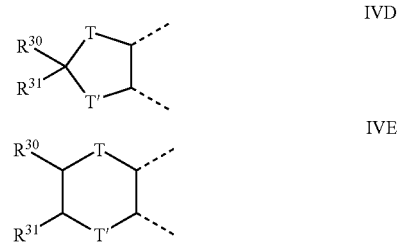

wherein T and T' may each independently be oxygen or the group —$NR^{26}$—, where $R^{26}$, $R^{30}$, and $R^{31}$ may be as set forth above.

Further, with reference to structure (III), $R^{18}$ and $R^{19}$ may each independently be, for example: hydrogen; hydroxy; $C_1$-$C_6$ alkyl; $C_3$-$C_7$ cycloalkyl; allyl; substituted or unsubstituted phenyl; substituted or unsubstituted benzyl; chloro; fluoro; the group —C(=O)W, wherein W may be, for example, hydrogen, hydroxy, $C_1$-$C_6$ alkyl, $C_1$-$C_6$ alkoxy, the unsubstituted, mono-or di-substituted aryl groups phenyl or naphthyl, phenoxy, mono- or di-($C_1$-$C_6$)alkoxy substituted phenoxy, mono- or di-($C_1$-$C_6$)alkoxy substituted phenoxy, amino, mono($C_1$-$C_6$)alkylamino, di($C_1$-$C_6$)alkylamino, phenylamino, mono- or di-($C_1$-$C_6$)alkyl substituted phenylamino, or mono- or di-($C_1$-$C_6$)alkoxy substituted phenylamino; —$OR^{33}$, wherein $R^{33}$ may be, for example, $C_1$-$C_6$ alkyl, phenyl($C_1$-$C_3$)alkyl, mono($C_1$-$C_6$)alkyl substituted phenyl($C_1$-$C_3$)alkyl, mono($C_1$-$C_6$)alkoxy substituted phenyl ($C_1$-$C_3$)alkyl, $C_1$-$C_6$ alkoxy($C_2$-$C_4$)alkyl, $C_3$-$C_7$ cycloalkyl, mono($C_1$-$C_4$)alkyl substituted $C_3$-$C_7$ cycloalkyl, $C_1$-$C_6$ chloroalkyl, $C_1$-$C_6$ fluoroalkyl, allyl, or the group —$CH(R^{34})W'$, wherein $R^{34}$ may be hydrogen or $C_1$-$C_3$ alkyl and W' may be CN, $CF_3$, or $COOR^{35}$, wherein $R^{35}$ may be hydrogen or $C_1$-$C_3$ alkyl, or $R^{33}$ may be the group, —C(=O)W", wherein W" may be, for example, hydrogen, $C_1$-$C_6$ alkyl, $C_1$-$C_6$ alkoxy, the unsubstituted, mono- or di-substituted aryl groups phenyl or naphthyl, phenoxy, mono-, or di-($C_1$-$C_6$)alkyl substituted phenoxy, mono- or di-($C_1$-$C_6$)alkoxy substituted phenoxy, amino, mono($C_1$-$C_6$)alkylamino, di($C_1$-$C_6$)alkylamino, phenylamino, mono- or di-($C_1$-$C_6$)alkyl substituted phenylamino, or mono- or di-($C_1$-$C_6$)alkoxy substituted phenylamino, wherein each of said phenyl, benzyl, or aryl group substituents may independently be $C_1$-$C_6$ alkyl or $C_1$-$C_6$ alkoxy; or a mono-substituted phenyl, said phenyl having a substituent located at the para position, wherein the substituent is: a dicarboxylic acid residue or derivative thereof, a diamine residue or derivative thereof, an amino alcohol residue or derivative thereof, a polyol residue or derivative thereof, —$CH_2$—, —$(CH_2)_t$—, or —$[O—(CH_2)_t]_k$—, wherein 't' is from an integer 2, 3, 4, 5 or 6 and 'k' is an integer from 1 to 50, the substituent being connected to an aryl group on another photochromic material. Alternatively, $R^{18}$ and $R^{19}$ together may form an oxo group, a spiro-carbocyclic group containing 3 to 6 carbon atoms, or a spiro-heterocyclic group containing 1 to 2 oxygen atoms and 3 to 6 carbon atoms including the spirocarbon atom, said spiro-carbocyclic and spiro-heterocyclic groups being annellated with 0, 1 or 2 benzene rings.

Referring still to structure (III), $R^{20}$ may be $-NR^{36}R^{37}$, wherein $R^{36}$ and $R^{37}$ may each independently be, for example, hydrogen, $C_1$-$C_6$ alkyl, $C_5$-$C_7$ cycloalkyl, phenyl, mono-substituted phenyl, or di-substituted phenyl, wherein said phenyl substituents are $C_1$-$C_6$ alkyl or $C_1$-$C_6$ alkoxy. Alternatively, $R^{36}$ and $R^{37}$ may come together with the nitrogen atom to form a nitrogen containing ring represented by the following graphic formula V:

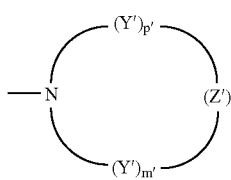

V wherein each —Y'— may independently be for each occurrence —$CH_2$—, —CH($R^{38}$)—, —C($R^{38}$)$_2$—, —CH(aryl)-, —C(aryl)$_2$-, or —C($R^{38}$)(aryl)-, and Z' may be —Y'—, —O—, —S—, —S(O)—, —$SO_2$—, —NH—, —N($R^{38}$)—, or —N(aryl)-, wherein each $R^{38}$ is independently $C_1$-$C_6$ alkyl, or hydroxy($C_1$-$C_6$)alkyl, each aryl is independently phenyl or naphthyl, m' is an integer 1, 2 or 3, and p' is an integer 0, 1, 2, or 3 and when p' is 0, Z' is —Y'—.

According to certain non-limiting embodiments, when $R^{20}$ is morpholino, $R^{16}$ may not be a 4-substituted piperidino attached to the 7-position of the indeno-fused naphthopyran skeleton.

According to certain non-limiting embodiments, the photochromic material may comprise a structure according to structure (III) where $R^{20}$ may comprise dialkylamino, morpholino, piperidino, substituted piperidino, pyrrolidino, substituted pyrrolidino, piperazino, or substituted piperazino. The substituent on the piperidino, pyrrolidino, or piperazino moiety may comprise ($C_1$-$C_6$) alkyl or hydroxy($C_1$-$C_6$)alkyl, such as, for example, hydroxymethyl. The alkyl substituents of the dialkylamino may be the same or different and may be $C_1$-$C_6$) alkyl.

According to still further non-limiting embodiments, the photochromic material may comprise a structure according to structure (III) where $R^{16}$ may be a fluoro group located at the 6-position of the indeno-fused naphthopyran of structure (III) and $R^{17}$ may comprise a second fluoro group located at the 11-position of the indeno-fused naphthopyran of structure (III).

Non-limiting methods of making the photochromic materials of various non-limiting embodiments of present disclosure will now be discussed with reference to FIGS. 1 and 2. Various methods to synthesize 7H-benzo[C]fluoren-5-ol compounds suitable for use in the present disclosure may be found, for example, in U.S. Pat. No. 6,296,785 at col. 11, line 6 to col. 28, line 35 and the examples; U.S. Pat. No. 5,645,767 at col. 6, lines 32 to col. 8, line 32 and the examples; U.S. application Ser. No. 11/102,280 (filed Apr. 8, 2005), paragraphs [0069] to [0072] and the examples; and U.S. application Ser. No. 11/102,279 (filed Apr. 8, 2005), paragraphs [0099] to [0106] and the examples, which disclosures are incorporated herein by reference.

For example, FIG. 1 illustrates one non-limiting reaction scheme for making 7H-benzo[C]fluoren-5-ol compounds which may, in certain non-limiting embodiments, have substituents R' and R", such as, for example a first and second electron-withdrawing group. The substituted and unsubstituted 7H-benzo[C]fluoren-5-ol compounds may then be further reacted, as depicted in FIG. 3, with a 1-(4-aminophenyl)-1-(4-fluorophenyl)-2-propyn-1-ol (the general synthesis of which is shown in FIG. 2), as described below, to form photochromic materials comprising a 3H,13H-indeno[2',3':3,4] naphtho[1,2-b]pyran (according to various non-limiting embodiments disclosed herein), further comprising a group B attached to the 3-position thereof and a group B' attached to the 3-position thereof, wherein the group B and group B' may be as defined and claimed herein. It will be appreciated that these reaction schemes are presented for illustration purposes only, and are not intended to be limiting herein. Additional examples of methods of making the photochromic materials according to various non-limiting embodiments disclosed herein are set forth in the Examples.

Referring now to FIG. 1, benzophenone 1, which may be substituted, for example, with a first substituent R' and/or a second substituent R", undergoes a Stobbe condensation with dimethyl succinate to give carboxylic acid 2, as a mixture of double bond isomers (when R' is not the same as R", the mixture of isomers may be separated at this point or taken directly on to subsequent reactions and separated later). Carboxylic acid 2 is reacted with acetic anhydride at elevated temperature to produce substituted naphthalene 3, where R* is acetate. The acetate is hydrolyzed to give naphthol 4 (R*=H). The ester of naphthol 4 is reacted with excess methyl magnesium bromide to give diol 5 upon aqueous workup. Diol 5 is cyclized with a sulfonic acid, such as, for example, dodecylbenzene sulfonic acid ("DBSA") to give the 7H-benzo[C]fluoren-5-ol 6.

Figure 2:
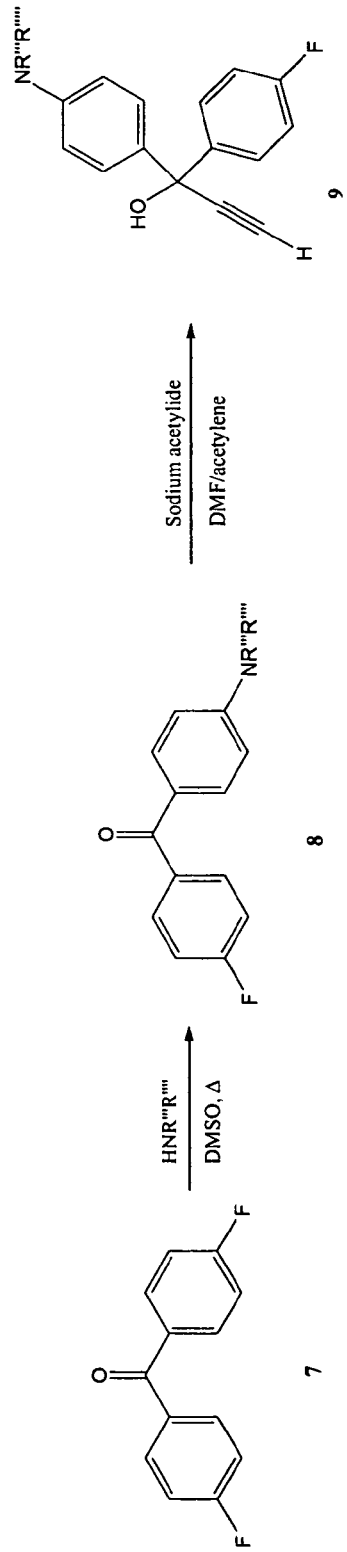
Figure 3:
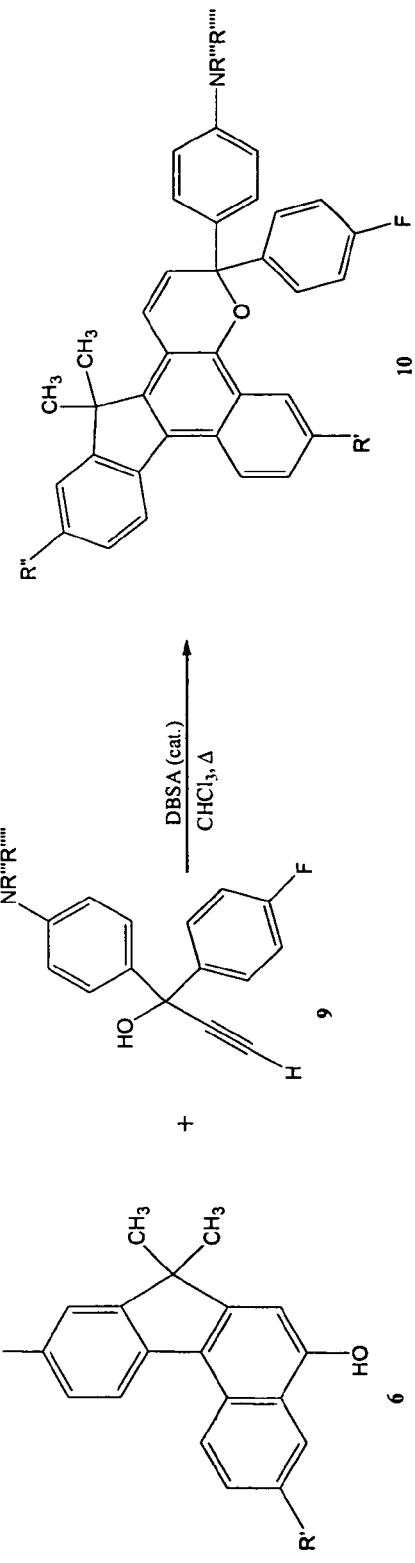
FIG. 3 illustrates a schematic diagram of a reaction scheme for making the photochromic materials according to various non-limiting embodiments disclosed herein.

Referring now to FIG. 2, wherein one non-limiting approach to the 1-(4-aminophenyl)-1-(4-fluorophenyl)-2-propyn-1-ol is presented, 4,4'-difluorobenzophenone (7) is reacted with a secondary amine HNR'''R'''' to give the 4-amino-4'-fluorobenzophenone 8, where R''' and R'''' may be the same as $R^{36}$ and $R^{37}$, respectively, as set forth and claimed herein. Acetylide anion, for example, sodium acetylide in acetylene saturated dimethylformamide, is added to the carbonyl of 4-amino-4'-fluorobenzophenone 8 to give, upon aqueous workup, 1-(4-aminophenyl)-1-(4-fluorophenyl)-2-propyn-1-ol 9.

Referring now to FIG. 3, 7H-benzo[C]fluoren-5-ol 6 (a synthesis of which is shown in FIG. 1) may be reacted with 1-(4-aminophenyl)-1-(4-fluorophenyl)-2-propyn-1-ol 9 (a synthesis of which is shown in FIG. 2). The condensation of 6 and 9 is catalyzed with a sulfonic acid, such as, for example DBSA or methane sulfonic acid, and affords 3H,13H-indeno [2',3':3,4]naphtho[1,2-b]pyran 10, according to various non-limiting embodiments of the present disclosure, comprising a group B attached to the 3-position thereof and a group B' attached to the 3-position thereof, wherein the group B and group B' may be as defined and claimed herein. One skilled in the art will recognize that various modifications to materials, reagents and/or reaction conditions may be made to the reaction schemes set forth in FIGS. 1-3 to afford the various non-limiting embodiments of the photochromic materials comprising substituted indeno-fused naphthopyrans, as set forth and claimed herein, and that such modifications are within the scope of the invention of the present disclosure.

As discussed above, the synthesis of the photochromic materials of the present disclosure may include reaction of a substituted or unsubstituted 7H-benzo[C]fluoren-5-ol 6 with a 1-(4-aminophenyl)-1-(4-fluorophenyl)-2-propyn-1-ol 9. Further, the amino group of the 1-(4-aminophenyl)-1-(4-fluorophenyl)-2-propyn-1-ol 9 may be substituted as set forth herein. According to certain non-limiting embodiments, the present disclosure provides for a chemical compound represented by the structure (VI):

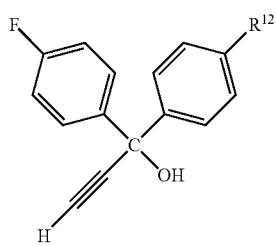

VI where group B may be a 4-fluorophenyl substituent and group B' represents a 4-substituted phenyl substituent where the substituent $R^{12}$ may be —$NR^{13}R^{14}$. According to certain non-limiting embodiments, $R^{13}$ and $R^{14}$ may each independently be hydrogen, $C_1$-$C_6$ alkyl, $C_5$-$C_7$ cycloalkyl, phenyl, mono-substituted phenyl, or di-substituted phenyl, wherein said phenyl substituents are $C_1$-$C_6$ alkyl or $C_1$-$C_6$ alkoxy. According to other non-limiting embodiments, $R^{13}$ and $R^{14}$ may come together with the nitrogen atom to form a nitrogen containing ring represented by the following graphic formula II:

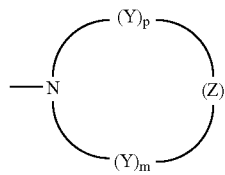

II wherein each —Y— may independently be chosen for each occurrence from —$CH_2$—, —$CH(R^{15})$—, —$C(R^{15})_2$—, —CH(aryl)-, —$C(aryl)_2$-, and —$C(R^{15})$(aryl)-, and Z is —Y—, —O—, —S—, —S(O)—, —$SO_2$—, —NH—, —$N(R^3)$—, or —N(aryl)-, wherein each $R^{15}$ may independently be, for example, $C_1$-$C_6$ alkyl, or hydroxy($C_1$-$C_6$)alkyl, each aryl may independently be phenyl or naphthyl, m is an integer 1, 2 or 3, and p is an integer 0, 1, 2, or 3, provided that when p is 0, Z is —Y.

According to certain non-limiting embodiments of 2-propyn-1-ol of structure VI, $R^{12}$ may comprise dialkylamino, morpholino, piperidino, substituted piperidino, pyrrolidino, substituted pyrrolidino, piperazino, or substituted piperazino. The substituents on the piperidino, pyrrolidino, or piperazino moiety may comprise, for example, ($C_1$-$C_6$) alkyl or hydroxy ($C_1$-$C_6$)alkyl. The alkyl substituents of the dialkylamino may be the same or different and may be ($C_1$-$C_6$) alkyl.

Certain other non-limiting embodiments of the photochromic materials of the present disclosure may be represented by their chemical name, as determined, at least in part, by the IUPAC system of nomenclature. Photochromic materials contemplated by the present disclosure include:
 (a) 3-(4-fluorophenyl)-3-(4-morpholinophenyl)-13,13-dimethyl-3H,13H-indeno[2',3':3,4]naphtho[1,2-b]pyran;
 (b) 3-(4-fluorophenyl)-3-(4-piperidinophenyl)-13,13-dimethyl-3H,13H-indeno[2',3':3,4]naphtho[1,2-b]pyran;
 (c) 3-(4-fluorophenyl)-3-(4-(2-methylpiperidino)phenyl)-13,13-dimethyl-3H,13H-indeno[2',3':3,4]naphtho[1,2-b]pyran;
 (d) 3-(4-fluorophenyl)-3-(4-piperazinophenyl)-13,13-dimethyl-3H,13H-indeno[2',3':3,4]naphtho[1,2-b]pyran;
 (e) 3-(4-fluorophenyl)-3-(4-pyrrolidinophenyl)-13,13-dimethyl-3H,13H-indeno[2',3':3,4]naphtho[1,2-b]pyran; and
 (f) 3-(4-fluorophenyl)-3-(4-(N,N-diethylamino)phenyl)-13,13-dimethyl-3H,13H-indeno[2',3':3,4]naphtho[1,2-b]pyran.

The photochromic materials of the present disclosure, for example, photochromic materials comprising an indeno-fused naphthopyran comprising a group B attached to the 3-position thereof and a group B' attached to the 3-position thereof, wherein the group B is a 4-fluorophenyl group and the group B' is a 4-substituted phenyl group, wherein the substituent in the 4-position of the 4-substituted phenyl group is —$NR^1R^2$, as set forth herein, may be used in those applications in which photochromic materials may be employed, such as, optical elements, for example, an ophthalmic element, a display element, a window, a mirror, an active liquid crystal cell element, or a passive liquid crystal cell element. As used herein, the term "optical" means pertaining to or associated with light and/or vision. As used herein, the term "ophthalmic" means pertaining to or associated with the eye and vision. As used herein, the term "display" means the visible or machine-readable representation of information in words, numbers, symbols, designs or drawings. Non-limiting examples of display elements include screens, monitors, and security elements, such as security marks. As used herein, the term "window" means an aperture adapted to permit the transmission of radiation therethrough. Non-limiting examples of windows include aircraft and automotive windshields, automotive and aircraft transparencies, e.g., T-roofs, sidelights and backlights, filters, shutters, and optical switches. As used herein, the term "mirror" means a surface that specularly reflects a large fraction of incident light. As used herein, the term "liquid crystal cell" refers to a structure containing a liquid crystal material that is capable of being ordered. One non-limiting example of a liquid crystal cell element is a liquid crystal display.

In certain non-limiting embodiments, the photochromic materials of the present disclosure may be used in an ophthalmic element, such as, corrective lenses, including single vision or multi-vision lenses, which may be either segmented or non-segmented multi-vision lenses (such as, but not limited to, bifocal lenses, trifocal lenses and progressive lenses), non-corrective lenses, a magnifying lens, a protective lens, a visor, goggles, and a lens for an optical instrument, such as a camera or telescope lens. In other non-limiting embodiments, the photochromic materials of the present disclosure may be used in plastic films and sheets, textiles, and coatings.

Further, it is contemplated that the photochromic materials according to various non-limiting embodiments disclosed herein may each be used alone, in combination with other photochromic materials according to various non-limiting embodiments disclosed herein, or in combination with an appropriate complementary conventional photochromic material. For example, the photochromic materials according to various non-limiting embodiments disclosed herein may be used in conjunction with conventional photochromic materials having activated absorption maxima within the range of about 400 to about 800 nanometers. Further, the photochromic materials according to various non-limiting embodiments disclosed herein may be used in conjunction with a complementary conventional polymerizable or a compatiblized photochromic material, such as for example, those disclosed in U.S. Pat. Nos. 6,113,814 (at col. 2, line 39 to col. 8, line 41), and 6,555,028 (at col. 2, line 65 to col. 12, line 56), which disclosures are hereby specifically incorporated by reference herein.

As discussed above, according to various non-limiting embodiments disclosed herein, the photochromic compositions may contain a mixture of photochromic materials. For example, although not limiting herein, mixtures of photochromic materials may be used to attain certain activated colors such as a near neutral gray or near neutral brown. See, for example, U.S. Pat. No. 5,645,767, col. 12, line 66 to col. 13, line 19, which describes the parameters that define neutral gray and brown colors and which disclosure is specifically incorporated by reference herein.

Various non-limiting embodiments disclosed herein provide a photochromic composition comprising an organic material, said organic material being at least one of polymeric material, an oligomeric material and a monomeric material, and a photochromic material according to any of the non-limiting embodiments of set forth above incorporated into at least a portion of the organic material. According to various non-limiting embodiments disclosed herein, the photochromic material may be incorporated into a portion of the organic material by at least one of blending and bonding the photochromic material with the organic material or a precursor thereof. As used herein with reference to the incorporation of photochromic materials into an organic material, the terms "blending" and "blended" mean that the photochromic material is intermixed or intermingled with the at least a portion of the organic material, but not bonded to the organic material. Further, as used herein with reference to the incorporation of photochromic materials into an organic material, the terms "bonding" or "bonded" mean that the photochromic material is linked to a portion of the organic material or a precursor thereof.

As discussed above, the photochromic compositions according to various non-limiting embodiments disclosed herein may comprise an organic material chosen from a polymeric material, an oligomeric material and/or a monomeric material. Examples of polymeric materials that may be used in conjunction with various non-limiting embodiments disclosed herein include, without limitation: polymers of bis (allyl carbonate) monomers; diethylene glycol dimethacrylate monomers; diisopropenyl benzene monomers; ethoxylated bisphenol A dimethacrylate monomers; ethylene glycol bismethacrylate monomers; poly(ethylene glycol) bismethacrylate monomers; ethoxylated phenol bismethacrylate monomers; alkoxylated polyhydric alcohol acrylate monomers, such as ethoxylated trimethylol propane triacrylate monomers; urethane acrylate monomers; vinylbenzene monomers; and styrene. Other non-limiting examples of suitable polymeric materials include polymers of polyfunctional, e.g., mono-, di- or multi-functional, acrylate and/or methacrylate monomers; poly($C_1$-$C_{12}$ alkyl methacrylates), such as poly(methyl methacrylate); poly(oxyalkylene) dimethacrylate; poly(alkoxylated phenol methacrylates); cellulose acetate; cellulose triacetate; cellulose acetate propionate; cellulose acetate butyrate; poly(vinyl acetate); poly (vinyl alcohol); poly(vinyl chloride); poly(vinylidene chloride); polyurethanes; polythiourethanes; thermoplastic polycarbonates; polyesters; poly(ethylene terephthalate); polystyrene; poly($\alpha$-methylstyrene); copolymers of styrene and methyl methacrylate; copolymers of styrene and acrylonitrile; polyvinylbutyral; and polymers of diallylidene pentaerythritol, particularly copolymers with polyol (allyl carbonate) monomers, e.g., diethylene glycol bis(allyl carbonate), and acrylate monomers, e.g., ethyl acrylate, butyl acrylate. Also contemplated are copolymers of the aforementioned monomers, combinations, and blends of the aforementioned polymers and copolymers with other polymers, e.g., to form interpenetrating network products.

Further, according to various non-limiting embodiments wherein transparency of the photochromic composition is desired, the organic material may be a transparent polymeric material. For example, according to various non-limiting embodiments, the polymeric material may be an optically clear polymeric material prepared from a thermoplastic polycarbonate resin, such as the resin derived from bisphenol A and phosgene, which is sold under the trademark, LEXAN®; a polyester, such as the material sold under the trademark, MYLAR®; a poly(methyl methacrylate), such as the material sold under the trademark, PLEXIGLAS®; and polymerizates of a polyol(allyl carbonate) monomer, especially diethylene glycol bis(allyl carbonate), which monomer is sold under the trademark CR-39®; and polyurea-polyurethane (polyurea urethane) polymers, which are prepared, for example, by the reaction of a polyurethane oligomer and a diamine curing agent, a composition for one such polymer being sold under the trademark TRIVEX® by PPG Industries, Inc. Other non-limiting examples of suitable polymeric materials include polymerizates of copolymers of a polyol (allyl carbonate), e.g., diethylene glycol bis(allyl carbonate), with other co-polymerizable monomeric materials, such as, but not limited to: copolymers with vinyl acetate, copolymers with a polyurethane having terminal diacrylate functionality, and copolymers with aliphatic urethanes, the terminal portion of which contain allyl or acrylyl functional groups. Still other suitable polymeric materials include, without limitation, poly (vinyl acetate), polyvinylbutyral, polyurethane, polythiourethanes, polymers chosen from diethylene glycol dimethacrylate monomers, diisopropenyl benzene monomers, ethoxylated bisphenol A dimethacrylate monomers, ethylene glycol bismethacrylate monomers, poly(ethylene glycol) bismethacrylate monomers, ethoxylated phenol bismethacrylate monomers and ethoxylated trimethylol propane triacrylate monomers, cellulose acetate, cellulose propionate, cellulose butyrate, cellulose acetate butyrate, polystyrene and co-polymers of styrene with methyl methacrylate, vinyl acetate and acrylonitrile. According to one non-limiting embodiment, the polymeric material may be optical resins sold by PPG Industries, Inc. under the CR-designation, such as, for example, CR-307, CR-407, and CR-607.

According to certain specific non-limiting embodiment, the organic material may be a polymeric material chosen from poly(carbonate), copolymers of ethylene and vinyl acetate; copolymers of ethylene and vinyl alcohol; copolymers of ethylene, vinyl acetate, and vinyl alcohol (such as those that result from the partial saponification of copolymers of ethylene and vinyl acetate); cellulose acetate butyrate; poly(urethane); poly(acrylate); poly(methacrylate); epoxies; aminoplast functional polymers; poly(anhydride); poly(urea urethane); N-alkoxymethyl(meth)acrylamide functional polymers; poly(siloxane); poly(silane); and combinations and mixtures thereof.

Various non-limiting embodiments disclosed herein provide photochromic articles comprising a substrate and a photochromic material according to any of the non-limiting embodiments discussed above connected to or incorporated into a portion of the substrate. As used herein, the term "connected to" means associated with, either directly or indirectly through another material or structure. In one non-limiting embodiment, the photochromic articles of the present disclosure may be an optical element, for example, but not limited to, an ophthalmic element, a display element, a window, a mirror, an active liquid crystal cell element, and a passive liquid crystal cell element. In certain non-limiting embodiments, the photochromic article is an ophthalmic element, for example, but not limited to, corrective lenses, including single vision or multi-vision lenses, which may be either segmented or non-segmented multi-vision lenses (such as, but not limited to, bifocal lenses, trifocal lenses and progressive lenses), non-corrective lenses, a magnifying lens, a protective lens, a visor, goggles, and a lens for an optical instrument.

According to various non-limiting embodiments disclosed herein wherein the substrate of the photochromic article comprises a polymeric material, the photochromic material may be connected to at least a portion of the substrate by incorporating the photochromic material into at least a portion of the polymeric material of the substrate, or at least a portion of the oligomeric or monomeric material from which the substrate is formed. For example, according to one non-limiting embodiment, the photochromic material may be incorporated into the polymeric material of the substrate by the cast-in-place method. Additionally or alternatively, the photochromic material may be incorporated into at least a portion of the polymeric material of the substrate by imbibition. Imbibition and the cast-in-place method are discussed below.

According to other non-limiting embodiments, the photochromic material may be connected to at least a portion of the substrate of the photochromic article as part of an at least partial coating that is connected to at least a portion of a substrate. According to this non-limiting embodiment, the substrate may be a polymeric substrate or an inorganic substrate (such as, but not limited to, a glass substrate). Further, the photochromic material may be incorporated into at least a portion of the coating composition prior to application of the coating composition to the substrate, or alternatively, a coating composition may be applied to the substrate, at least partially set, and thereafter the photochromic material may be imbibed into at least a portion of the coating. As used herein, the terms "set" and "setting" include, without limitation, curing, polymerizing, cross-linking, cooling, and drying.

For example, in one non-limiting embodiment of the present disclosure, the photochromic article may comprise an at least partial coating of a polymeric material connected to at least a portion of a surface thereof. According to this non-limiting embodiment, the photochromic material may be blended and/or bonded with at least a portion of the polymeric material of the at least partial coating.

The at least partial coating comprising a photochromic material may be directly connected the substrate, for example, by directly applying a coating composition comprising a photochromic material to at least a portion of a surface of the substrate, and at least partially setting the coating composition. Additionally or alternatively, the at least partial coating comprising a photochromic material may be connected to the substrate, for example, through one or more additional coatings. For example, while not limiting herein, according to various non-limiting embodiments, an additional coating composition may be applied to at least a portion of the surface of the substrate, at least partially set, and thereafter the coating composition comprising a photochromic material may be applied over the additional coating and at least partially set. Non-limiting methods of applying coatings compositions to substrates are discussed herein below.

Non-limiting examples of additional coatings and films that may be used in conjunction with the photochromic articles disclosed herein include primer or compatiblizing coatings; protective coatings, including transitional coatings, abrasion-resistant coatings and other coating that protect against the effects of polymerization reaction chemicals and/or protect against deterioration due to environmental conditions such as moisture, heat, ultraviolet light, oxygen (e.g., UV-shielding coatings and oxygen barrier-coatings); anti-reflective coatings; conventional photochromic coating; and polarizing coatings and polarizing stretched-films; and combinations thereof.

Non-limiting examples of primer or compatiblizing coatings that may be used in conjunction with various non-limiting embodiments disclosed herein include coatings comprising coupling agents, at least partial hydrolysates of coupling agents, and mixtures thereof. As used herein "coupling agent" means a material having a group capable of reacting, binding and/or associating with a group on a surface. Coupling agents according to various non-limiting embodiments disclosed herein may include organometallics such as silanes, titanates, zirconates, aluminates, zirconium aluminates, hydrolysates thereof and mixtures thereof. As used herein the phrase "at least partial hydrolysates of coupling agents" means that some to all of the hydrolyzable groups on the coupling agent are hydrolyzed. Other non-limiting examples of primer coatings that are suitable for use in conjunction with the various non-limiting embodiments disclosed herein include those primer coatings described U.S. Pat. No. 6,025,026 at col. 3, line 3 to col. 11, line 40 and U.S. Pat. No. 6,150,430 at col. 2, line 39 to col. 7, line 58, which disclosures are hereby specifically incorporated herein by reference.

As used herein, the term "transitional coating" means a coating that aids in creating a gradient in properties between two coatings. For example, although not limiting herein, a transitional coating may aid in creating a gradient in hardness between a relatively hard coating (such as an abrasion-resistant coating) and a relatively soft coating (such as a photochromic coating). Non-limiting examples of transitional coatings include radiation-cured, acrylate-based thin films as described in U.S. Patent Application Publication 2003/0165686 at paragraphs [0079]-[0173], which are hereby specifically incorporated by reference herein.

As used herein the term "abrasion-resistant coating" refers to a protective polymeric material that demonstrates a resistance to abrasion that is greater than a standard reference material, e.g., a polymer made of CR-39® monomer available from PPG Industries, Inc, as tested in a method comparable to ASTM F-735 Standard Test Method for Abrasion Resistance of Transparent Plastics and Coatings Using the Oscillating Sand Method. Non-limiting examples of abrasion-resistant coatings include abrasion-resistant coatings comprising organosilanes, organosiloxanes, abrasion-resistant coatings based on inorganic materials such as silica, titania and/or zirconia, and organic abrasion-resistant coatings of the type that are ultraviolet light curable.

Non-limiting examples of antireflective coatings include a monolayer, multilayer coatings of metal oxides, metal fluorides, or other such materials, which may be deposited onto the articles disclosed herein (or onto self supporting films that are applied to the articles), for example, through vacuum deposition, sputtering, etc.

Non-limiting examples of conventional photochromic coatings include, but are not limited to, coatings comprising conventional photochromic materials.

Non-limiting examples of polarizing coatings and polarizing stretched-films include, but are not limited to, coatings (such as those described in U.S. Patent Application Publication No. 2005/0151926), and stretched-films comprising dichroic compounds that are known in the art.

As discussed herein, according to various non-limiting embodiments, an additional at least partial coating or film may be formed on the substrate prior to forming the coating comprising the photochromic material according to various non-limiting embodiments disclosed herein on the substrate. For example, according to certain non-limiting embodiments a primer or compatibilizing coating may be formed on the substrate prior to applying the coating composition comprising the photochromic material. Additionally or alternatively, an additional at least partial coating may be formed on the substrate after forming coating comprising the photochromic material according to various non-limiting embodiments disclosed herein on the substrate, for example, as an overcoating on the photochromic coating. For example, according to certain non-limiting embodiments, a transitional coating may be formed over the coating comprising the photochromic material, and an abrasion-resistant coating may be formed over the transitional coating.

For example, according to one non-limiting embodiment there is provided a photochromic article comprising a substrate (such as, but not limited to a plano-concave or a plano-convex ophthalmic lens substrate), which comprises an abrasion-resistant coating on at least a portion of a surface thereof; a primer or compatiblizing coating on at least a portion of the abrasion-resistant coating; a photochromic coating comprising a photochromic material according to various non-limiting embodiments disclosed herein on at least a portion of the primer or compatiblizing coating; a transitional coating on at least a portion of the photochromic coating; and an abrasion-resistant coating on at least a portion of the transitional coating. Further, according to this non-limiting embodiment, the photochromic article may also comprise, for example, an antireflective coating that is connected to a surface of the substrate and/or a polarizing coating or film that is connected to a surface of the substrate.

Non-limiting methods of making photochromic compositions and photochromic articles, such as optical elements, according to various non-limiting embodiments disclosed herein will now be discussed. One non-limiting embodiment provides a method of making a photochromic composition, the method comprising incorporating a photochromic material into at least a portion of an organic material. Non-limiting methods of incorporating photochromic materials into an organic material include, for example, mixing the photochromic material into a solution or melt of a polymeric, oligomeric, or monomeric material, and subsequently at least partially setting the polymeric, oligomeric, or monomeric material (with or without bonding the photochromic material to the organic material); and imbibing the photochromic material into the organic material (with or without bonding the photochromic material to the organic material).

Another non-limiting embodiment provides a method of making a photochromic article comprising connecting a photochromic material according to various non-limiting embodiments discussed above to at least a portion of a substrate. For example, if the substrate comprises a polymeric material, the photochromic material may be connected to at least a portion of the substrate by at least one of the cast-in-place method and by imbibition. For example, in the cast-in-place method, the photochromic material may be mixed with a polymeric solution or melt, or other oligomeric and/or monomeric solution or mixture, which are subsequently cast into a mold having a desired shape and at least partially set to form the substrate. Optionally, according to this non-limiting embodiment, the photochromic material may be bonded to a portion of the polymeric material of the substrate, for example, by co-polymerization with a monomeric precursor thereof. In the imbibition method, the photochromic material may be diffused into the polymeric material of the substrate after it is formed, for example, by immersing a substrate in a solution containing the photochromic material, with or without heating. Thereafter, although not required, the photochromic material may be bonded with the polymeric material.

Other non-limiting embodiments disclosed herein provide a method of making an optical element comprising connecting a photochromic material to at least a portion of a substrate by at least one of in-mold casting, coating and lamination. For example, according to one non-limiting embodiment, wherein the substrate comprises a polymeric material, the photochromic material may be connected to at least a portion of a substrate by in-mold casting. According to this non-limiting embodiment, a coating composition comprising the photochromic material, which may be a liquid coating composition or a powder coating composition, is applied to the surface of a mold and at least partially set. Thereafter, a polymer solution or melt, or oligomeric or monomeric solution or mixture is cast over the coating and at least partially set. After setting, the coated substrate is removed from the mold. Non-limiting examples of powder coatings in which the photochromic materials according to various non-limiting embodiments disclosed herein may be employed are set forth in U.S. Pat. No. 6,068,797 at col. 7, line 50 to col. 19, line 42, which disclosure is hereby specifically incorporated by reference herein.

According to still another non-limiting embodiment, wherein the substrate comprises a polymeric material or an inorganic material such as glass, the photochromic material may be connected to at least a portion of a substrate by coating. Non-limiting examples of suitable coating methods include spin coating, spray coating (e.g., using a liquid or powder coating), curtain coating, roll coating, spin and spray coating, over-molding, and combinations thereof. For example, according to one non-limiting embodiment, the photochromic material may be connected to the substrate by over-molding. According to this non-limiting embodiment, a coating composition comprising the photochromic material (which may be a liquid coating composition or a powder coating composition as previously discussed) may be applied to a mold and then the substrate may be placed into the mold such that the substrate contacts the coating causing it to spread over at least a portion of the surface of the substrate. Thereafter, the coating composition may be at least partially set and the coated substrate may be removed from the mold. Alternatively, over-molding may be done by placing the substrate into a mold such that an open region is defined between the substrate and the mold, and thereafter injecting a coating composition comprising the photochromic material into the open region. Thereafter, the coating composition may be at least partially set and the coated substrate may be removed from the mold.

Additionally or alternatively, a coating composition (with or without a photochromic material) may be applied to a substrate (for example, by any of the foregoing methods), the coating composition may be at least partially set, and thereafter, a photochromic material may be imbibed (as previously discussed) into the coating composition.

According to yet another non-limiting embodiment, wherein the substrate comprises a polymeric material or an inorganic material such as glass, the photochromic material may be connected to at least a portion of a substrate by lamination. According to this non-limiting embodiment, a film comprising the photochromic material may be adhered or otherwise connect to a portion of the substrate, with or without an adhesive and/or the application of heat and pressure. Thereafter, if desired, a second substrate may be applied over the first substrate and the two substrates may be laminated together (i.e., by the application of heat and pressure) to form an element wherein the film comprising the photochromic material is interposed between the two substrates. Methods of forming films comprising a photochromic material may include for example and without limitation, combining a photochromic material with a polymeric solution or oligomeric solution or mixture, casting or extruding a film therefrom, and, if required, at least partially setting the film. Additionally or alternatively, a film may be formed (with or without a photochromic material) and imbibed with the photochromic material (as discussed above).

Further, various non-limiting embodiments disclosed herein contemplate the use of various combinations of the forgoing methods to form photochromic articles according to various non-limiting embodiments disclosed herein. For example, and without limitation herein, according to one non-limiting embodiment, a photochromic material may be connected to substrate by incorporation into an organic material from which the substrate is formed (for example, using the cast-in-place method and/or imbibition), and thereafter a photochromic material (which may be the same or different from the aforementioned photochromic material) may be connected to a portion of the substrate using the in-mold casting, coating and/or lamination methods discussed above.

Further, it will be appreciated by those skilled in the art that the photochromic compositions and articles according to various non-limiting embodiments disclosed herein may further comprise other additives that aid in the processing and/or performance of the composition or article. Non-limiting examples of such additives include photoinitiators, thermal initiators, polymerization inhibitors, solvents, light stabilizers (such as, but not limited to, ultraviolet light absorbers and light stabilizers, such as hindered amine light stabilizers (HALS)), heat stabilizers, mold release agents, rheology control agents, leveling agents (such as, but not limited to, surfactants), free radical scavengers, adhesion promoters (such as hexanediol diacrylate and coupling agents), and combinations and mixtures thereof.

According to various non-limiting embodiments, the photochromic materials described herein may be used in amounts (or ratios) such that the organic material or substrate into which the photochromic materials are incorporated or otherwise connected exhibits desired optical properties. For example, the amount and types of photochromic materials may be selected such that the organic material or substrate may be clear or colorless when the photochromic material is in the closed-form (i.e., in the bleached or unactivated state) and may exhibit a desired resultant color when the photochromic material is in the open-form (that is, when activated by actinic radiation). The precise amount of the photochromic material to be utilized in the various photochromic compositions and articles described herein is not critical provided that a sufficient amount is used to produce the desired effect. It should be appreciated that the particular amount of the photochromic material used may depend on a variety of factors, such as but not limited to, the absorption characteristics of the photochromic material, the color and intensity of the color desired upon activation, and the method used to incorporate or connect the photochromic material to the substrate. Although not limiting herein, according to various non-limiting embodiments disclosed herein, the amount of the photochromic material that is incorporated into an organic material may range from 0.01 to 40 weight percent based on the weight of the organic material.

Various non-limiting embodiments disclosed herein will now be illustrated in the following non-limiting examples.

EXAMPLES

In Part I of the Examples, the synthetic procedures used to make photochromic materials according to certain non-limiting embodiments disclosed herein are set forth in Examples 1-4. In Part II, the formation of methacrylate test chips incorporating certain photochromic materials as described herein, along with comparative photochromic materials, and testing procedures to determine fade rate ($T_{1/2}$), maximum absorbance wavelength, and saturated optical density are described.

Part I: Synthetic Procedures

Example 1

Step 1

Piperidine (23.4 grams ("g")), 4,4'-difluorobenzophenone (60 g), triethylamine (30.6 g) were added to a reaction flask containing 100 milliliters ("mL") of dimethylsulfoxide. The resulting mixture was heated to 105° C. and stirred overnight under a nitrogen atmosphere. After 24 hours at 105° C., the reaction was quenched into 1400 mL of water with vigorous stirring to see a light brown solid precipitate out. The solid was filtered, washed with water and dried open to air to obtain 79.5 g of the desired product, 4-fluoro-4'-piperidinobenzophenone. This material was used in the next step without further purification.

Step 2

The product of Step 1, 4-fluoro-4'-piperidinobenzophenone (78 g) was added to a reaction flask containing 500 mL of N,N-dimethylformamide saturated with acetylene. The resulting mixture was stirred using a mechanical stirrer at room temperature under a nitrogen atmosphere. Sodium acetylide in xylenes/mineral oil (73.5 g of a 18% by weight solution) was added over thirty minutes to the reaction mixture while stirring. After stirring for one hour at room temperature, the reaction was quenched into 4 L of water with vigorous stirring to see a yellow brown solid precipitate out. The solid was filtered, washed with water and dried open to air to obtain 85 g of the desired product, 1-(4-fluorophenyl)-1-(4-piperidinophenyl)-2-propyn-1-ol. This material was used in Step 7 without further purification.

Step 3

Potassium t-butoxide (68.8 g) was weighed into a reaction flask equipped with a mechanical stirrer, placed under a nitrogen atmosphere and 700 mL of toluene was added followed by 4,4'-difluorobenzophenone (100 g). The reaction mixture was stirred mechanically and heated to 70° C. A solution of dimethyl succinate (80 g) in 100 mL of toluene was added to the reaction mixture over a 60 minute period. The reaction mixture was heated at 70° C. for 4 hours. After cooling to room temperature, the reaction mixture was poured into 500 mL of water and the toluene layer discarded. The aqueous layer was extracted with diethyl ether (1×400 mL) to remove the neutral products, and then acidified the aqueous layer with concentrated HCl. A brownish-yellow oily solid was obtained from the aqueous layer, and was extracted with 3×300 mL of ethyl acetate. The organic layers were combined, washed with saturated NaCl solution (1×500 mL) and dried over anhydrous sodium sulfate. Removal of the solvent by rotary evaporation yielded 122 g of 4,4-di(4-fluorophenyl))-3- methoxycarbonyl-3-butenoic acid as a brownish oily solid. This material was not purified further but was used directly in the next step.

Step 4

The product of Step 3 (4,4-di(4-fluorophenyl))-3-methoxycarbonyl-3-butenoic acid, 122 g) and acetic anhydride (250 mL) were added to a reaction flask. The reaction mixture was heated to reflux for 5 hours under a nitrogen atmosphere. The reaction mixture was cooled to room temperature and subsequently poured into 1200 mL of water. The resulting precipitate was collected by vacuum filtration and washed with cold water yielding 110 g of 1-(4-fluorophenyl)-2-methoxycarbonyl-4-acetoxy-6-fluoronaphthalene. The product was used without further purification in the subsequent reaction.

Step 5

1-(4-Fluorophenyl)-2-methoxycarbonyl-4-acetoxy-6-fluoronaphthalene from Step 4 (110 g) and 400 mL of methanol were combined in a reaction flask. Added 5 mL of concentrated hydrochloric acid to the reaction flask, and heated to reflux for 4 hours under a nitrogen atmosphere. The reaction mixture was cooled to room temperature and then to 0° C. White crystals of the desired product (1-(4-fluorophenyl)-2-methoxycarbonyl-4-hydroxy-6-fluoronaphthalene, 65 g) were obtained, and subsequently filtered off and dried under vacuum. This material was not purified further but was used directly in the next step.

Step 6

The product of Step 5 (1-(4-fluorophenyl)-2-methoxycarbonyl-4-hydroxy-6-fluoronaphthalene, 39.4 g) was added to a reaction flask containing 300 mL of tetrahydrofuran. The resulting mixture was cooled in an ice water bath and stirred under a nitrogen atmosphere. 167 mL of a methyl magnesium bromide solution (3M in diethyl ether) was added dropwise over thirty minutes. The resulting yellow reaction mixture was warmed to room temperature, and stirred overnight. The reaction mixture was poured into 400 mL of water, and neutralized with concentrated HCl until acidic. The mixture was extracted with three 300 mL portions of ether, and the organic portions were combined and washed with 1 L of saturated NaCl solution. The organic layer was dried over anhydrous sodium sulfate and concentrated by rotary evaporation. The resulting brown oil (37.8 g) was transferred into a reaction vessel (fitted with a Dean-Stark trap) containing 300 mL of xylene to which five drops of dodecylbenzene sulfonic acid were added. The reaction mixture was heated to reflux for 3 hours and cooled. The xylene was removed via rotary evaporation to yield 35 g of 3,9-difluoro-7,7-dimethyl-5-hydroxy-7H-benzo[C]fluorine as a light brown oil. This material was not purified further but was used directly in the next step.

Step 7

The product of Step 6 (3,9-difluoro-7,7-dimethyl-5-hydroxy-7H-benzo[C]fluorene, 5.55 g), the product of Step 2 (1-(4-fluorophenyl)-1-(4-piperdinophenyl)-2-propyn-1-ol, 5.8 g), 8 drops of methane sulfonic acid and 250 mL of chloroform were combined in a reaction flask and stirred at reflux temperatures under a nitrogen atmosphere. After two hours, an additional 3.0 g of the 1-(4-fluorophenyl)-1-(4-piperidinophenyl)-2-propyn-1-ol and 8 drops of dodecyl benzene sulfonic acid were added to the reaction mixture. The reaction mixture was heated at 50° C. overnight, and then cooled to room temperature. The reaction mixture was washed carefully with a mixture of 250 mL of a saturated sodium bicarbonate solution and 250 mL of water. The organic layer was separated, dried over sodium sulfate, and concentrated by rotary evaporation. The residue was chromatographed on a silica gel column using a mixture of hexane and ethyl acetate (95/5) as the eluant. Photochromic fractions were collected and concentrated by rotary evaporation to obtain a bluish-white solid (8.0 g). The bluish-white foam was further purified by precipitation from methanol to yield 3.5 g of a greenish white solid. An NMR spectrum showed the product to have a structure consistent with 3-(4-fluorophenyl)-3-(4-piperidinophenyl)-6,11-difluoro-113,13-dimethyl-3H,13H-indeno[2',3':3,4]naphtho[1,2-b]pyran.

Example 2

Step 1

The product of Example 1, Step 2 in U.S. Pat. No. 5,645,767 (1-phenyl-2-methoxycarbonyl-4-acetoxynaphthalene, 50 g) was added to a reaction flask containing 500 mL of tetrahydrofuran. The resulting mixture was cooled in an ice water bath and stirred under a nitrogen atmosphere. 703 mL of a methyl magnesium chloride solution (1M in tetrahydrofuran) was added dropwise over forty-five minutes. The resulting yellow reaction mixture was stirred at 0° C. for 2 hours and slowly warmed to room temperature. The reaction mixture was poured into 2 L of an ice/water mixture. Ethyl ether (1 L) was added, and the layers separated. The aqueous layer was extracted with two 500 mL portions of ether, and the organic portions were combined and washed with 1 L of water. The organic layer was dried over anhydrous sodium sulfate and concentrated by rotary evaporation. The resulting oil was transferred into a reaction vessel (fitted with a Dean-Stark trap) containing 500 mL of toluene to which ten drops of dodecylbenzene sulfonic acid were added. The reaction mixture was heated to reflux for 2 hours and cooled. The toluene was removed via rotary evaporation to yield 40.2 g of a light yellow solid. An NMR spectrum showed the product to have a structure consistent with 7,7-dimethyl-5-hydroxy-7H-benzo[C]fluorene. This material was not purified further but was used directly in the next step.

Step 2

The product of Step 1, 7,7-dimethyl-5-hydroxy-7H-benzo[C]fluorene (6.0 g), the product of Example 1, Step 2 1-(4-fluorophenyl)-1-(4-piperidinophenyl)-2-propyn-1-ol (7.1 g), seven drops of methane sulfonic acid and 250 mL of chloroform were combined in a reaction flask and stirred at reflux temperatures. After two hours, an additional 2.0 g of 1-(4-fluorophenyl)-1-(4-piperidinophenyl)-2-propyn-1-ol and four drops of methane sulfonic acid was added to the reaction mixture. This was followed by another 1.0 g addition of the 1-(4-fluorophenyl)-1-(4-piperidinophenyl)-2-propyn-1-ol and four drops of methane sulfonic acid after another two hours. The reaction mixture was heated at reflux for 6 hours and then cooled to room temperature. The reaction mixture was washed carefully with a mixture of 200 mL of a saturated sodium bicarbonate solution and 200 mL of water. The organic layer was separated, dried over sodium sulfate, and concentrated by rotary evaporation. The residue was chromatographed on a silica gel column using a mixture of hexane and ethyl acetate (93/7) as the eluant. Photochromic fractions were collected and concentrated by rotary evaporation to obtain a bluish solid (11 g). The blue solid was further purified by crystallization from a 1:1 mixture of diethyl ether and hexane to yield 9.2 g of a white solid. An NMR spectrum showed the product to have a structure consistent with 3-(4- fluorophenyl)-3-(4-piperidinophenyl)-13,13-dimethyl-3H, 13H-indeno[2',3':3,4]naphtho[1,2-b]pyran.

Example 3

The product of Example 1, Step 6 (3,9-difluoro-7,7-dimethyl-5-hydroxy-7H-benzo[C]fluorene, 5.0 g), 1-(4-fluorophenyl)-1-(4-morpholinophenyl)-2-propyn-1-ol (5.3 g), 7 drops of methane sulfonic acid and 200 mL of chloroform were combined in a reaction flask and stirred at reflux temperatures under a nitrogen atmosphere. After one hour, an additional 5.0 g of the 1-(4-fluorophenyl)-1-(4-morpholinophenyl)-2-propyn-1-ol was added to the reaction mixture and the heating continued. After two hours, an additional 2.0 g of the 1-(4-fluorophenyl)-1-(4-morpholinophenyl)-2-propyn-1-ol and 4 drops of methane sulfonic acid were added to the reaction mixture. The reaction mixture was heated for another four hours, and then cooled to room temperature. The reaction mixture was washed carefully with a mixture of 125 mL of a saturated sodium bicarbonate solution and 125 mL of water. The organic layer was separated, dried over sodium sulfate, and concentrated by rotary evaporation. The residue was chromatographed on a silica gel column using a mixture of hexane, methylene chloride and ethyl acetate (60/35/5) as the eluant. Photochromic fractions were collected and concentrated by rotary evaporation to obtain a blue solid (4.0 g). The blue solid was further purified by crystallization from a 1:1 mixture of diethyl ether and hexane to yield 3.4 g of a white solid. An NMR spectrum showed the product to have a structure consistent with 3-(4-fluorophenyl)-3-(4-morpholinophenyl)-6,11-difluoro-13,13-dimethyl-3H,13H-indeno[2',3':3,4]naphtho[1,2-b]pyran.

Example 4

The product of Example 2, Step 1, 7,7-dimethyl-5-hydroxy-7H-benzo[C]fluorene (4.0 g), 1-(4-fluorophenyl)-1-(4-morpholinophenyl)-2-propyn-1-ol (6.3 g), 8 drops of methane sulfonic acid and 200 mL of chloroform were combined in a reaction flask and stirred at reflux temperatures under a nitrogen atmosphere. After one hour, an additional 4.6 g of the 1-(4-fluorophenyl)-1-(4-morpholinophenyl)-2-propyn-1-ol was added to the reaction mixture and the heating continued. After two hours, an additional 5.0 g of the 1-(4-fluorophenyl)-1-(4-morpholinophenyl)-2-propyn-1-ol and 4 drops of methane sulfonic acid were added to the reaction mixture. The reaction mixture was heated overnight, and then cooled to room temperature. The reaction mixture was washed carefully with a mixture of 100 mL of a saturated sodium bicarbonate solution and 100 mL of water. The organic layer was separated, dried over sodium sulfate, and concentrated by rotary evaporation. The residue was chromatographed on a silica gel column using a mixture of hexane, methylene chloride and ethyl acetate (60/37/3) as the eluant. Photochromic fractions were collected and concentrated by rotary evaporation to obtain a blue solid (8.2 g). The blue solid was further purified by crystallization from diethyl ether to yield 4.4 g of a white solid. An NMR spectrum showed the product to have a structure consistent with 3-(4-fluorophenyl)-3-(4-morpholinophenyl)-13,13-dimethyl-3H, 13H-indeno[2',3':3,4]naphtho[1,2-b]pyran.

Part II: Testing

The photochromic performance of the photochromic materials of Examples 1-4, and Comparative Example CE1-CE6 were tested using the following optical bench set-up. In addition, a fifth compound according to certain non-limiting embodiments of the present disclosure, Example 5, was tested. It will be appreciated by those skilled in the art that the photochromic materials of Example 5 and Comparative Examples CE1-CE6 may be made in accordance with the teachings and examples disclosed herein with appropriate modifications, which will be readily apparent to those skilled in the art upon reading the present disclosure. Further, those skilled in the art will recognize that various modifications to the disclosed methods, as well as other methods, may be used in making the photochromic materials of Examples 1-4 without deviating from the scope of the present disclosure as set forth in the specification and claims herein.

Methacrylate Chip Procedure

A quantity of the photochromic material to be tested, calculated to yield a $1.5 \times 10^{-3}$ M solution was added to a flask containing 50 g of a monomer blend of 4 parts ethoxylated bisphenol A dimethacrylate (BPA 2EO DMA), 1 part poly (ethylene glycol) 600 dimethacrylate, and 0.033 weight percent 2,2'-azobis(2-methyl propionitrile) ("AIBN"). The photochromic material was dissolved into the monomer blend by stirring and gentle heating. After a clear solution was obtained, it was vacuum degassed before being poured into a flat sheet mold having the interior dimensions of 2.2 mm×6 inches (15.24 cm)×6 inches (15.24 cm). The mold was sealed and placed in a horizontal air flow, programmable oven programmed to increase the temperature from 40° C. to 95° C. over a 5 hour interval, hold the temperature at 95° C. for 3 hours, and then lower the temperature to 60° C. for at least 2 hours. After the mold was opened, the polymer sheet was cut using a diamond blade saw into 2 inch (5.1 cm) test squares.

The test squares incorporating the photochromic materials prepared as described above were tested for photochromic response on an optical bench. Prior to testing on the optical bench, the photochromic test squares were exposed to 365 nm ultraviolet light for about 15 minutes to cause the photochromic materials therein to transform from the unactivated ground (or bleached) state to an activated (or colored) state, and then placed in a 75° C. oven for about 15 minutes to allow the photochromic material to revert back to the unactivated state. The test squares were then cooled to room temperature, exposed to fluorescent room lighting for at least 2 hours, and then kept covered (that is, in a dark environment) for at least 2 hours prior to testing on an optical bench maintained at 23° C. The bench was fitted with a 300-watt xenon arc lamp, a remote controlled shutter, a Melles Griot KG2 filter that modifies the UV and IR wavelengths and acts as a heat-sink, neutral density filter(s), and a sample holder, situated within a 23° C. water bath, in which the square to be tested was inserted. A collimated beam of light from a tungsten lamp was passed through the square at a small angle (approximately 30°) normal to the square. After passing through the square, the light from the tungsten lamp was directed to a collection sphere, where the light was blended, and on to an Ocean Optics S2000 spectrometer where the spectrum of the measuring beam was collected and analyzed. The $\lambda_{max\text{-}vis}$ is the wavelength in the visible spectrum at which the maximum absorption of the activated (colored) form of the photochromic material in the test square occurs. The $\lambda_{max\text{-}vis}$ wavelength was determined by testing the photochromic test squares in a Varian Cary 4000 UV-Visible spectrophotometer. The output signals from the detector were processed by a radiometer.

The saturated optical density ("Sat'd OD") for each test square was determined by opening the shutter from the xenon lamp and measuring the transmittance after exposing the test chip to UV radiation for 30 minutes. The $\lambda_{max\text{-}vis}$ at the Sat'd OD was calculated from the activated data measured by the S2000 spectrometer on the optical bench. The Fade Rate, as measured by the fade half life (i.e., $T_{1/2}$), is the time interval in seconds for the absorbance of the activated form of the photochromic material in the test squares to reach one half of the Sat'd OD absorbance value at room temperature (23° C.), after removal of the source of activating light. Performance Rating ("PR") is calculated from the Sat'd OD and $T_{1/2}$ by the equation:

$PR=((\text{Sat'd OD})/T_{1/2} \times 10{,}000.$

Photochromic data of certain photochromic materials according to the present disclosure are presented in Table 1. Photochromic data for comparative photochromic materials (i.e. photochromic indeno-fused naphthopyrans wherein the groups B and B', combined, are not a 4-fluorophenyl group and a 4-aminophenyl group, as set forth herein) are presented in Table 2.

TABLE 1

Photochromic Materials and Test Results

| Ex. | Photochromic Material | $\lambda_{max\text{-}vis}$ (nm) | Sat'd OD | $T_{1/2}$ (sec) | PR |
|---|---|---|---|---|---|
| 1 | 3-(4-fluorophenyl)-3-(4-piperidinophenyl)-6,11-difluoro-13,13-dimethyl-3H,13H-indeno[2',3':3,4]naphtho[1,2-b]pyran | 613 | 0.48 | 64 | 75 |
| 2 | 3-(4-fluorophenyl)-3-(4-piperidinophenyl)-13,13-dimethyl-3H,13H-indeno[2',3':3,4]naphtho[1,2-b]pyran | 595 | 0.97 | 118 | 82 |
| 3 | 3-(4-fluorophenyl)-3-(4-morpholinophenyl)-6,11-difluoro-13,13-dimethyl-3H,13H-indeno[2',3':3,4]naphtho[1,2-b]pyran | 595 | 0.58 | 74 | 78 |
| 4 | 3-(4-fluorophenyl)-3-(4-morpholinophenyl)-13,13-dimethyl-3H,13H-indeno[2',3':3,4]naphtho[1,2-b]pyran | 579 | 1.06 | 151 | 70 |
| 5 | 3-(4-fluorophenyl)-3-(4-(2-methylpiperidino)phenyl)-13,13-dimethyl-3H,13H-indeno[2',3':3,4]naphtho[1,2-b]pyran | 603 | 1.01 | 124 | 82 |

TABLE 2

Comparative Photochromic Materials and Test Results

| Ex. | Photochromic Material | $\lambda_{max\text{-}vis}$ (nm) | Sat'd OD | $T_{1/2}$ (sec) | PR |
|---|---|---|---|---|---|
| CE1 | 3,3-diphenyl-13,13-dimethyl-3H,13H-indeno[2',3':3,4]naphtho[1,2-b]pyran | 532 | 1.50 | 723 | 21 |
| CE2 | 3-phenyl-3-(4-piperidinophenyl)-6,11-difluoro-13,13-dimethyl-3H,13H-indeno[2',3':3,4]naphtho[1,2-b]pyran | 616 | 0.73 | 94 | 78 |
| CE3 | 3-phenyl-3-(4-piperidinophenyl)-13,13-dimethyl-3H,13H-indeno[2',3':3,4]naphtho[1,2-b]pyran | 599 | 1.04 | 180 | 50 |
| CE4 | 3-(4-morpholinophenyl)-3-phenyl-6,11-difluoro-13,13-dimethyl-3H,13H-indeno[2',3':3,4]naphtho[1,2-b]pyran | 599 | 0.84 | 122 | 69 |
| CE5 | 3-(4-morpholinophenyl)-3-phenyl-13,13-dimethyl-3H,13H-indeno[2',3':3,4]naphtho[1,2-b]pyran | 583 | 1.45 | 241 | 60 |
| CE6 | 3-(4-fluorophenyl)-3-phenyl-13,13-dimethyl-3H,13H-indeno[2',3':3,4]naphtho[1,2-b]pyran | 533 | 1.53 | 542 | 28 |

It is to be understood that the present description illustrates aspects of the invention relevant to a clear understanding of the invention. Certain aspects of the invention that would be apparent to those of ordinary skill in the art and that, therefore, would not facilitate a better understanding of the invention have not been presented in order to simplify the present description. Although the present invention has been described in connection with certain embodiments, the present invention is not limited to the particular embodiments disclosed, but is intended to cover modifications that are within the spirit and scope of the invention, as defined by the appended claims.

What is claimed is:

1. A photochromic material comprising an indeno-fused naphthopyran having a 4-fluorophenyl group and a 4-substituted phenyl group at the 3-position of the indeno-fused naphthopyran, which can be represented by the structure:

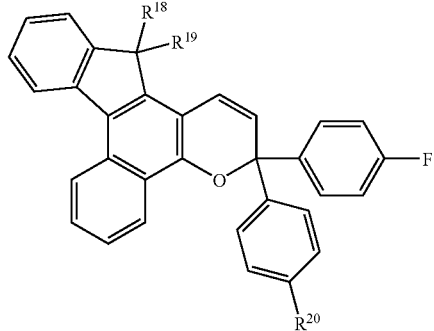

III wherein $R^{18}$ and $R^{19}$ are each independently: hydrogen; hydroxy; $C_1$-$C_6$ alkyl; $C_3$-$C_7$ cycloalkyl; allyl; substituted or unsubstituted phenyl; substituted or unsubstituted benzyl; chloro; fluoro; the group —C(=O)W, wherein W is hydrogen, hydroxy, $C_1$-$C_6$ alkyl, $C_1$-$C_6$ alkoxy, the unsubstituted, mono-or di-substituted aryl groups phenyl or naphthyl, phenoxy, mono- or di-(-$C_1$-$C_6$)alkoxy substituted phenoxy, mono- or di-($C_1$-$C_6$)alkoxy substituted phenoxy, amino, mono($C_1$-$C_6$)alkylamino, di($C_1$-$C_6$)alkylamino, phenylamino, mono- or di-(—$C_1$-$C_6$) alkyl substituted phenylamino, or mono- or di-(—$C_1$-$C_6$)alkoxy substituted phenylamino; —$OR^{33}$, wherein $R^{33}$ is $C_1$-$C_6$ alkyl, phenyl($C_1$-$C_3$)alkyl, mono($C_1$-$C_6$) alkyl substituted phenyl($C_1$-$C_3$)alkyl, mono($C_1$-$C_6$) alkoxy substituted phenyl($C_1$-$C_3$)alkyl, $C_1$-$C_6$ alkoxy ($C_2$-$C_4$)alkyl, $C_3$-$C_7$ cycloalkyl, mono($C_1$-$C_4$)alkyl substituted $C_3$-$C_7$ cycloalkyl, $C_1$-$C_6$ chloroalkyl, $C_1$-$C_6$ fluoroalkyl, allyl, or the group —CH(R$^{34}$)W', wherein R$^{34}$ is hydrogen or C$_1$-C$_3$ alkyl and W' is CN, CF$_3$, or COOR$^{35}$, wherein R$^{35}$ is hydrogen or C$_1$-C$_3$ alkyl, or R$^{33}$ is the group, —C(=O)W''', wherein W''' is hydrogen, C$_1$-C$_6$ alkyl, C$_1$-C$_6$ alkoxy, the unsubstituted, mono- or di-substituted aryl groups phenyl or naphthyl, phenoxy, mono-, or di-(—C$_1$-C$_6$)alkyl substituted phenoxy, mono- or di-(C$_1$-C$_6$)alkoxy substituted phenoxy, amino, mono(C$_1$-C$_6$)alkylamino, di(C$_1$-C$_6$)alkylamino, phenylamino, mono- or di-(C$_1$-C$_6$)alkyl substituted phenylamino, or mono- or di-(C$_1$-C$_6$)alkoxy substituted phenylamino, wherein each of said phenyl, benzyl, or aryl group substituents are independently C$_1$-C$_6$ alkyl or C$_1$-C$_6$ alkoxy; or a mono-substituted phenyl, said phenyl having a substituent located at the para position, wherein the substituent is: a dicarboxylic acid residue or derivative thereof, a diamine residue or derivative thereof, an amino alcohol residue or derivative thereof, a polyol residue or derivative thereof, —CH$_2$—, —(CH$_2$)$_t$—, or —[O—(CH$_2$)$_t$]$_k$—, wherein t is an integer 2, 3, 4, 5 or 6 and k is an integer from 1 to 50, the substituent being connected to an aryl group on another photochromic material; or R$^{18}$ and R$^{19}$ together form an oxo group, a spiro-carbocyclic group containing 3 to 6 carbon atoms, or a spiro-heterocyclic group containing 1 to 2 oxygen atoms and 3 to 6 carbon atoms including the spirocarbon atom, said spiro-carbocyclic and spiro-heterocyclic groups being annellated with 0, 1 or 2 benzene rings; and R$^{20}$ is —NR$^{36}$R$^{37}$, wherein R$^{36}$ and R$^{37}$ are each independently hydrogen, C$_1$-C$_6$ alkyl, C$_5$-C$_7$ cycloalkyl, phenyl, mono-substituted phenyl, or di-substituted phenyl, wherein said phenyl substituents are C$_1$-C$_6$ alkyl or C$_1$-C$_6$ alkoxy, or R$^{36}$ and R$^{37}$ come together with the nitrogen atom to form a nitrogen containing ring represented by the following graphic formula V:

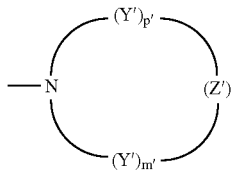

V wherein each —Y'— is independently chosen for each occurrence from —CH$_2$—, —CH(R$^{38}$)—, —C(R$^{38}$)$_2$—, —CH(aryl)-, —C(aryl)$_2$-, and —C(R$^{38}$)(aryl)-, and Z' is —Y'—, —O—, —S—, —S(O)—, —SO$_2$—, —NH—, —N(R$^{38}$)—, or —N(aryl)-, wherein each R$^{38}$ is independently C$_1$-C$_6$ alkyl, or hydroxy(C$_1$-C$_6$)alkyl, each aryl is independently phenyl or naphthyl, m' is an integer 1, 2 or 3, and p' is an integer 0, 1, 2, or 3, provided that when p' is 0, Z' is —Y'—.

2. The photochromic material of claim 1, wherein said photochromic material has a faster fade rate than a comparable indeno-fused naphthopyran that lacks a 4-fluorophenyl group and a 4-substituted phenyl group at the 3-position thereof, and wherein the substituent of the 4-substituted phenyl group is —NR$^{36}$R$^{37}$.

3. The photochromic material of claim 2, wherein the 4-substituted phenyl group is chosen from 4-morpholinophenyl, 4-(N,N-dialkylamino)phenyl, 4-piperidinophenyl, 4-(substituted piperidino)phenyl, 4-pyrrolidinophenyl, 4-(substituted pyrrolidino)phenyl, 4-piperazinophenyl, or 4-(substituted piperazino)phenyl, wherein the substituent on the piperidino, pyrrolidino, or piperazino comprises (C$_1$-C$_6$) alkyl or hydroxy(C$_1$-C$_6$)alkyl and the alkyl groups of the dialkylamino are the same or different.

4. The photochromic material of claim 1, wherein R$^{20}$ comprises dialkylamino, morpholino, piperidino, substituted piperidino, pyrrolidino, substituted pyrrolidino, piperazino, or substituted piperazino, wherein the substituent on the piperidino, pyrrolidino, or piperazino comprises (C$_3$-C$_6$) alkyl or hydroxy(C$_1$-C$_6$)alkyl and the alkyl groups of the dialkylamino are, the same or different.

5. The photochromic material of claim 4 wherein R$^{18}$ and R$^{19}$ are each independently: hydrogen; hydroxy; C$_1$-C$_6$ alkyl; C$_3$-C$_7$ cycloalkyl; allyl; or substituted or unsubstituted phenyl, said phenyl substituents being chosen from C$_1$-C$_6$ alkyl or C$_1$-C$_6$ alkoxy.

6. The photochromic material of claim 4 wherein R$^{18}$ and R$^{19}$ are each independently C$_1$-C$_6$ alkyl.

7. The photochromic material of claim 1 which is chosen from:
(a)  3-(4-fluorophenyl)-3-(4-morpholinophenyl)-13,13-dimethyl-3H,13H-indeno[2',3':3,4]naphtha[1,2-b]pyran;
(b)  3-(4-fluorophenyl)-3-(4-piperidinophenyl)-13,13-dimethyl-3H,13H-indeno[2',3':3,4]naphtho[1,2-b]pyran;
(c) 3-(4-fluorophenyl)-3-(4-(2-methylpiperidino)phenyl)-13,13-dimethyl-3H,13H-indeno[2',3':3,4]naphtho[1,2-b]pyran;
(d)  3-(4-fluorophenyl)-3-(4-piperazinophenyl)-13,13-dimethyl-3H,13H-indeno[2',3':3,4]naphtho[1,2-b]pyran;
(e)  3-(4-fluorophenyl)-3-(4-pyrrolidinophenyl)-13,13-dimethyl-3H,13H-indeno[2',3':3,4]naphtho[1,2-b]pyran; and
(f)  3-(4-fluorophenyl)-3-(4-(N,N-diethylamino)phenyl)-13,13-dimethyl-3H,13H-indeno[2',3':3,4]naphtho[1,2-b]pyran.

8. A photochromic article comprising:
a substrate; and
the photochromic material according to claim 1 connected to at least a portion of the substrate.

9. The photochromic article of claim 8, wherein the photochromic article is an optical element, said optical element being at least one of an ophthalmic element, a display element, a window, a mirror, an active liquid crystal cell element, or a passive liquid crystal cell element.

10. The photochromic article of claim 8, wherein the substrate comprises a polymeric material and the photochromic material is incorporated into at least a portion of the polymeric material by at least one method chosen from blending the photochromic material with at least a portion of the polymeric material, bonding the photochromic material to at least a portion of the polymeric material, and imbibing the photochromic material into at least a portion of the polymeric material.

11. The photochromic article of claim 10 wherein the polymeric material is chosen from polymerizates of diethylene glycol bis(allyl carbonate), thermoplastic polycarbonate resin, polyester, and polyurea urethane polymers.

12. The photochromic article of claim 8, wherein the photochromic article comprises an at least partial coating connected to at least a portion of the substrate, the at least partial coating comprising the photochromic material.

13. A chemical compound represented by the structure:

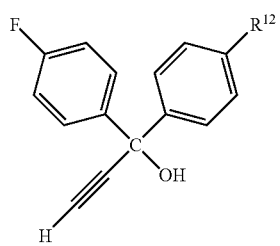

VI wherein $R^{12}$ is $-NR^{13}R^{14}$, wherein $R^{13}$ and $R^{14}$ are each independently hydrogen, $C_1$-$C_6$ alkyl, $C_5$-$C_7$ cycloalkyl, phenyl, mono-substituted phenyl, or di-substituted phenyl, wherein said phenyl substituents are $C_1$-$C_6$ alkyl or $C_1$-$C_6$ alkoxy, or $R^{13}$ and $R^{14}$ come together with the nitrogen atom to form a nitrogen containing ring represented by the following graphic formula II:

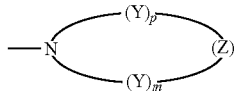

wherein each —Y— is independently chosen for each occurrence from $-CH_2-$, $-CH(R^{15})-$, $-C(R^{15})_2-$, $-CH(aryl)-$, $-C(aryl)_2-$, and $-C(R_{15})(aryl)-$, and Z is —Y—, —O—, —S—, —S(O)—, —SO$_2$—, —NH—, —N($R^{15}$)—, or —N(aryl)-, wherein each $R^{15}$ is independently $C_1$-$C_6$ alkyl, or hydroxy($C_1$-$C_6$)alkyl, each aryl is independently phenyl or naphthyl, m is the integer 1, 2 or 3, and p is the integer 0, 1, 2, or 3, provided that when p is 0, Z is —Y—.

14. The chemical compound of claim 13, wherein $R^{12}$ comprises dialkylamino, morpholino, piperidino, substituted piperidino, pyrrolidino, substituted pyrrolidino, piperazino, or substituted piperazino, wherein the substituent on the piperidino, pyrrolidino, or piperazino comprises ($C_1$-$C_6$) alkyl or hydroxy($C_1$-$C_6$)alkyl and the alkyl groups of the dialkylamino are, the same or different, ($C_1$-$C_6$) alkyl.

* * * * *